United States Patent [19]

Imamura

[11] 4,272,634
[45] Jun. 9, 1981

[54] PROCESS FOR THE PRODUCTION OF INTERMEDIATE OXIDATION PRODUCTS OF TOLUENES HAVING ETHER LINKAGES

[75] Inventor: Juichi Imamura, Chofu, Japan

[73] Assignees: Director-General of Agency of Industrial Science and Technology; Sanko Chemical Co., Ltd.; Nippon Soda Co., Ltd., all of Tokyo, Japan

[21] Appl. No.: 102,559

[22] Filed: Dec. 11, 1979

Related U.S. Application Data

[62] Division of Ser. No. 863,954, Dec. 23, 1977, Pat. No. 4,220,605.

[30] Foreign Application Priority Data

Dec. 27, 1976 [JP] Japan .................................. 51-158756
Dec. 27, 1976 [JP] Japan .................................. 51-158757
Aug. 15, 1977 [JP] Japan .................................. 52-97646

[51] Int. Cl.³ ........................ C07C 45/00; C07C 37/00
[52] U.S. Cl. ...................................... 568/432; 568/648
[58] Field of Search ...................... 568/648, 431, 432

[56] References Cited

U.S. PATENT DOCUMENTS 3,665,030 5/1972 d'Ostrowick et al. ........... 568/648 X
4,113,782 9/1978 Imamura et al. ................. 260/600 R Primary Examiner—Bernard Helfin

[57] ABSTRACT

A process for the production of alcohols and/or aldehydes which comprises subjecting a toluene derivative having an ether linkage or linkages of the general formula:

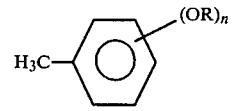

wherein RO is an ether grouping where R stands for a hydrocarbyl group with 1~20 carbon atoms which may carry an inert substituent or substituents and n stands for an integer of 1~2, to auto-oxidation with molecular oxygen in liquid phase to form the corresponding alcohol and/or aldehyde, characterized in that the reaction is carried out by using a lower saturated fatty acid and/or an anhydride thereof as solvent in the presence of a soluble cobalt salt and a bromine ion-supplying substance at a reaction temperature ranging from 30° C. to 200° C. in such manner that the conversion rate of the toluene derivative does not exceed 90%.

5 Claims, No Drawings

PROCESS FOR THE PRODUCTION OF INTERMEDIATE OXIDATION PRODUCTS OF TOLUENES HAVING ETHER LINKAGES

This is a division of application Ser. No. 863,954 filed Dec. 23, 1977 and now U.S. Pat. No. 4,220,605.

BACKGROUND OF THE INVENTION

The present invention relates to a process for the production of intermediate oxidation products such as benzyl alcohols and/or benzaldehydes having ether linkages. More particularly, the present invention relates to a process for the production of alcohols and/or aldehydes wherein a toluene having an ether linkage or linkages is oxidized in liquid phase with molecular oxygen for selectively oxidizing the methyl group bound to the benzene ring to hydroxymethyl group or formyl group to convert the toluene into the corresponding alcohol and/or aldehyde.

Benzyl alcohol and benzaldehyde derivatives having ether linkages are useful as perfumes, medicaments and starting materials for other fine chemicals. In particular, m-phenoxybenzaldehyde is very important as an intermediate product for agricultural and horticultural agents. However, the production of these compounds in a good yield is extremely difficult. Up to the present, therefore, an industrial synthetic process as contemplated in the present invention wherein the methyl group of a toluene having an ether linkage or linkages is oxidized in liquid phase with molecular oxygen has not yet been developed. At the present time, an oxidation process wherein an oxidizing reagent such as a permanganate is used is exclusively considered to be industrially advantageous (German Pat. No. 1,953,258).

It is generally known that when a methylated aromatic compound is oxidized with molecular oxygen in liquid phase in the presence of a Redox catalyst, the methyl group of the aromatic compound is converted by oxidation into carboxyl group via hydroxymethyl and formyl groups. In this oxidation process, however, the rate of oxidizing formyl group to carboxyl group is much faster than that of oxidizing methyl group to formyl group. Thus, the production of formyl (aldehyde) compounds in a good yield is extremely difficult according to this oxidation process. For this reason, there has not yet been proposed an industrially operable process for preparing formylated aromatic compounds in a good yield by oxidizing methylated aromatic compounds in liquid phase with molecular oxygen.

With a view to overcoming difficulty in conversion of the methyl group bound to the aromatic ring into formyl group, the present inventor has made extensive researches on auto-oxidation of toluene derivatives in liquid phase with molecular oxygen. As a result of the extensive researches, it has now been found that when a toluene having an ether linkage or linkages is subjected to auto-oxidation conducted by the aid of a relatively large amount of a heavy metal salt, especially a cobalt salt as catalyst in the presence of a lower saturated fatty acid and/or an anhydride thereof, an aldehyde is chiefly formed under the reaction condition using excess oxygen but an alcohol is chiefly formed under the reaction condition using insufficient oxygen. However, this process is effective for oxidation of the methyl group of a toluene having an ether group in p-position but is still unsatisfactory for oxidation of the methyl group of a toluene having an ether group in m- or p-position thereof. In case an ether group is present in m- or p-position to the methyl group of toluene, the reaction velocity in oxidation of such toluene derivative is extremely reduced as compared with the case of oxidizing a toluene having an ether group in p-position thereof, so that the reaction is not initiated under low oxygen pressure nor promoted smoothly even under high oxygen pressure unless severe conditions are adopted. As side reactions take place inevitably under such severe conditions, however, decomposition of the ether linkage tends to occur, thus often resulting in interruption of the reaction. Thus, oxidation of the m- and o-compounds is attended by such disadvantages that a slight change in the reaction conditions induces a significant variation in the result of experiments and that the rate of selection to the end product is considerably reduced as compared with the case of oxidizing the p-compounds. In the case of oxidizing the m- and o-compounds, only a very small amount of impurities causes significant variation in the results of experiments. These disadvantages are apparently shown as bad reproducibility in experiments. This phenomenon is noticeable in the case of the m-compounds which are most difficult to oxidize. For instance, the liquid phase oxidation of m-phenoxytoluene under pressure of oxygen gives as the best result 68% in conversion rate and 35 mol% in the rate of selection to m-phenoxybenzaldehyde. In many cases, however, the reaction did not proceed, or if proceeded, the reaction was interrupted at the stage of 10 mol% or less in the conversion rate even if the reactions were carried out under the same reaction conditions. Thus, the rate of selection was less than 10 mol% in the majority of the cases.

Although many studies were made to explain the reason why reproducibility is not good in the oxidation of the m- and o-compounds, the present inventor failed to reach a persuasive conclusion. As a result of further studies on the stable methods for oxidation, the present inventor found that a process wherein cobalt and nickel ions are used as catalyst or wherein cerium ion is allowed to be coexistent with the catalyst is effective for stable oxidation. However, the result of actual experiments for the m- and o-compounds was not so good. In the case of m-phenoxytoluene, for instance, m-phenoxybenzaldehyde was obtained with good reproducibility but only at 20% in conversion rate and 13~17 mol% in rate of selection. As a result of the present inventor's further researches on addition of a third component to the catalyst to improve the above process, it has now been found surprisingly that the existence of a very small amount of a bromine ion-supplying substance in the reaction system is very effective for selective conversion of such hardly oxidizable methyl group in the m- and o-compounds into formyl group. The present invention has been accomplished on the basis of the above finding.

A process for the oxidation of hardly oxidizable compounds wherein a bromine compound is added to the liquid phase auto-oxidation system for methylbenzenes where a cobalt salt in acetic acid is used as catalyst is well known as a process for producing terephthalic acid and is now operated in a large commercial scale. However, no information has been reported on the example for remarkably increasing the rate of selection of intermediate oxidation products by adding a very small amount of a bromine compound to such system. According to the present inventor's study, it has been recognized that intermediate oxidation products such as aldehydes can be produced at a high rate of selection by (a) adding a very small amount of a bromine compound to the liquid phase auto-oxidation system for alkyl or aryl ethers of m-cresol under normal pressure where a cobalt salt is used as catalyst and acetic acid is used as solvent and (b) limiting the conversion rate to 60% or less, in particular 50% or less. In case the bromine compound is absent in the reaction system, the reaction does not take place even under the same reaction condition. Even when the reaction is forced to take place by adding a reaction initiator to the reaction system, the rate of selection to the intermediate oxidation products is only 10 mol% or less at a conversion rate of 20~30%. Considering the result of above experiments, the effects achieved by the present invention are indeed surprising and are not believable from the common knowledge in this art.

BRIEF SUMMARY OF THE INVENTION

Accordingly, it is a prime object of the present invention to provide an industrially advantageous process for the production of alcohols and/or aldehydes wherein a toluene having an ether linkage or linkages is used as starting material and is subjected to auto-oxidation with molecular oxygen to convert the material into the corresponding intermediate oxidation products, i.e. alcohols and/or aldehydes.

It is another object of the present invention to provide a process for aromatic alcohols and/or aldehydes as intermediate oxidation products with good reproducibility and in a high rate of selection and high yield wherein occurrence of side reactions causing decomposition of ether linkage is inhibited in the liquid phase auto-oxidation of toluenes having ether groups with molecular oxygen so as to promote the auto-oxidation smoothly.

Other objects, features and merits of the present invention will be apparent more fully from the following description.

DETAILED DESCRIPTION OF THE INVENTION

In accordance with the present invention, there is provided a process for the production of alcohols and/or aldehydes which comprises subjecting a toluene derivative having an ether linkage or linkages of the general formula:

wherein RO is an ether grouping where R stands for a hydrocarbyl group with 1~20 carbon atoms which may carry an inert substituent or substituents and n stands for an integer of 1~2, to an auto-oxidation reaction in liquid phase with molecular oxygen to form the corresponding alcohol and/or aldehyde, characterized in that the oxidation reaction is carried out by using a lower saturated fatty acid and/or an anhydride thereof as solvent in the presence of a soluble cobalt salt and a bromine ion-supplying substance at a reaction temperature ranging from 30° C. to 200° C. in such manner that the conversion rate of the toluene derivative does not exceed 90%.

In the toluene derivative of the general formula utilizable in the process of this invention, the hydrocarbyl group with 1~20 carbon atoms are generally selected from the group consisting of alkyl, cycloalkyl, aryl and aralkyl groups which may be substituted by one or more substituents inert to the oxidation reaction. Illustrative of the hydrocarbyl group are alkyl groups such as methyl, ethyl, n-propyl, isopropyl, n-hexyl, n-octyl and isooctyl groups; cycloalkyl groups such as cyclohexyl, cyclooctyl, methylcyclohexyl and ethylcyclohexyl groups; aryl groups such as phenyl, tolyl, xylyl, ethylphenyl, n-propylphenyl, isopropylphenyl, butylphenyl and naphthyl groups and aralkyl groups such as benzyl and phenethyl groups.

In the present invention, these hydrocarbyl groups may be substituted by one or more inert substituents which give no trouble to the oxidation reaction. Illustrative of the inert substituents in this case are hydrocarbyloxy groups with 1~10 carbon atoms such as methoxy, ethoxy, n-propoxy, isopropoxy, n-butoxy, n-octyloxy, cyclohexyloxy and similar cycloalkyloxy, phenoxy and benzyloxy groups; hydrocarbyloxycarbonyl groups such as methoxycarbonyl, ethoxycarbonyl, n-propoxycarbonyl, isopropoxycarbonyl, n-butoxycarbonyl and n-octyloxycarbonyl groups; and halogen atoms such as chlorine and bromine atoms. These inert substituents may further be substituted by a similar inert substituent or substituents. Hydrocarbyl groups substituted by one or more reactive substituents such as hydroxyl, mercapto and amino groups which disturb the oxidation reaction are inappropriate as the hydrocarbyl group R. The free hydroxyl or mercapto group possesses auto-oxidation-inhibiting action and strongly inhibits proceeding of the oxidation reaction of the present invention.

In the present invention, the oxidation reactivity of the toluene derivative having the ether grouping RO becomes poor and decomposition of the starting compound (destroy of the ether linkage) tends to occur as the hydrocarbyl group R becomes complicate. Thus, the reaction does not take place unless reaction conditions capable of promoting the reaction smoothly at low temperatures are chosen. The effect achieved by addition of the bromine compound becomes remarkable as the structure of the starting compound becomes complicate. In the case of the starting compound having too complicate structure, however, synthesis of such starting compound will be difficult and moreover reactivity and selectivity of such starting compound will be decreased even when the bromine compound is added, probably because of decomposition reactions prevailing over the oxidation reaction for such complicate compound. Actually, therefore, the number of carbon atoms constituting the hydrocarbyl group R is preferably limited to 12 or less. The beneficial effect achieved by addition of the bromine compound becomes significant when the starting compound having phenyl, cyclohexyl, m-tolyl or a linear alkyl group of $C_1 \sim C_8$ as the hydrocarbyl group R is used.

The term "bromine ion-supplying substance" is used herein to mean a substance capable of being dissolved in the reaction liquid and supplying bromine ion to the reaction system and is sometimes referred to herein simply as "bromine compound" or "bromine ion donor." Examples of the bromine ion-supplying substance include, in addition to bromine itself, various inorganic and organic bromine compounds. The fact that organic bromides such as bromobenzene and alkyl bromides exhibit excellent results will be evident from Examples given hereinafter. However, an extremely remarkable effect is attained by the use of an inorganic bromide such as hydrogen bromide, an alkali metal bromide or an alkali earth metal bromide. In view of solubility, cost and easiness in handling, the use of potassium bromide or sodium bromide which are easily commercially available is most advantageous in the present invention as bromine ion donor. The amount of the bromine ion-supplying substance is generally within the range of 0.0001~0.5 mol, especially 0.001~0.3 mol per mol of the starting compound. If the amount is smaller then the above range, the beneficial effect achieved by the bromine ion donor will not be recognized. On the other hand, if the amount is too excessive, the amount of carboxylic acid will be increased in proportion to decrease in the rate of selection to intermediate oxidation products and at the same time the amount of organobromine compounds formed as by-products will become larger, thus resulting in such defect that the cost for separating and purifying the desired product will be increased significantly. It is also important to limit the amount of the bromine ion-supplying substance in proportion to the amount of the cobalt salt added. The amount of the bromine ion-supplying substance is preferably limited within the range of 0.001~10 mols, especially 0.005~5 mols per mol of the cobalt salt. If the amount of the bromine ion-supplying substance is smaller than the above range, the beneficial effect achieved by addition of the substance will not be recognized. On the other hand, if the amount is larger than the above range, the induction period for the reaction will significantly be increased with considerable decrease in the rate of selection to the desired product.

In the present invention, at least one lower saturated fatty acid and/or at least one anhydride thereof functioning as both reaction promotor and reaction solvent is added to the reaction system. The term "lower saturated fatty acid" is used herein to mean a saturated aliphatic carboxylic acid with 2~8 carbon atoms. Preferable examples of the lower saturated fatty acid include acetic acid, propionic acid, n-butyric acid and isobutyric acid. Especially preferable reaction solvent in practice of the present invention are acetic acid and acetic anhydride. Halogenated lower saturated fatty acids, i.e. lower saturated fatty acids substituted by halogen such as chlorine or bromine are also included in the category of the lower saturated fatty acids utilizable for the present invention. However, the use of such halogenated lower saturated fatty acids is less recommendable because of their cost and difficulty in handling. In the present invention, a reaction solvent utilizable for conventional oxidative reactions may be used in addition to the lower saturated fatty acid or an anhydride thereof. Preferable examples of such reaction solvent include aromatic hydrocarbons such as benzene and toluene and the corresponding halogenated derivatives. Besides these, any organic solvent can be used so far as it is inert to the oxidation reaction. The organic solvent which is inert to the oxidation reaction and can replace a part of the reaction solvent is used in an amount of at most 80% by weight based on the total reaction solvent.

The catalyst used in the present invention is one or more soluble salts of cobalt. In the reaction solvent, such cobalt salt produces cobalt ion which is then coordinated with the lower saturated fatty acid or an anhydride thereof and functions as an effective catalyst for synthetizing alcohols and aldehydes. In the present invention, any of the soluble salts of cobalt can be used so far as it is soluble in the solvent and capable of producing in the reaction liquid the cobalt ion containing the lower saturated fatty acid or an anhydride thereof as ligand. Illustrative of the cobalt salt are, for example, inorganic cobalt salts such as cobalt chloride, cobalt bromide, cobalt hydroxide and cobalt nitrate and organic cobalt salts such as cobalt acetate, cobalt propionate, cobalt stearate, cobalt naphthenate, cobalt acetylacetonate and cobalt benzoate. A cobalt halide may not be regarded as a preferable catalyst as the reaction often does not take place by the use of such cobalt halide alone. As is evident from Examples, however, the conjoint use of cobalt bromide and sodium acetate exhibits excellent effects on oxidation which are almost equivalent to the case of using cobalt acetate together with sodium bromide. Thus, a cobalt halide can be used in the present invention as the effective catalyst so far as it can be replaced partly or wholly in the reaction system with the lower saturated fatty acid.

The quantity of the solvent varies according to the sort of solvent, the reaction conditions adopted and the sort of compound to be oxidized but is generally within the range of 0.2~20 mols per mol of the starting compound. Especially preferable range of the quantity of the solvent is 2~15 mols per mol of the starting compound. If the quantity of the solvent is too small, the character of the present invention will be lost, thus resulting in considerable decrease in reaction velocity and in the rate of selection of the desired products, and in the extreme case, the reaction often does not take place. On the other hand, the use of an excessive amount of the solvent gives no significant influence on the oxidation reaction. In certain cases, the maximum rate of selection can be obtained in the case of using the solvent in an amount of at least 15 mols per mol of the starting compound. However, the use of the solvent in a great excess amount rather incurs various disadvantages including slowdown of the oxidation velocity, reduction in productivity of the desired products and increase in the optimum amount of the catalyst and in the cost for after-treatment of the reaction liquid.

The optimum amount of the catalyst varies according to the reaction conditions including the sorts of starting compounds, solvents and bromine compounds, the reaction temperature adopted and the sort of the solvent used, but is generally at least 0.001 mol, preferably at least 0.01 mol per mol of the starting compound. The catalyst is advantageously used in an amount within the range of 0.05~0.3 mol per mol of the starting compound. Thus, the maximum amount of the catalyst can be regarded as the saturating solubility of the catalyst in the reaction liquid under the reaction condition adopted. If the amount of the catalyst added is smaller than the above range, both the reaction velocity and the rate of selection to the desired product will be reduced. The reaction will not be initiated when the amount of the catalyst is too small. On the other hand, the use of the catalyst in an amount larger than the above range gives no substantial minus effect against the reaction except some influence on the aspect of reaction technology. However, the use of an extremely excess amount of the catalyst is not preferable for the reason that a large amount of the catalyst will be precipitated in the reaction liquid on separation of the end product to decrease the yield of the end product.

In order to produce substituted benzaldehydes and/or substituted benzyl alcohols in a good yield according to the process of this invention, it is essential to use a lower saturated fatty acid with 2~8 carbon atoms and/or an anhydride thereof as the solvent for the reaction. Acetic acid is particularly suitable as the lower saturated fatty acid and acetic anhydride as the lower saturated fatty acid anhydride. The use of a mixture of acetic acid and acetic anhydride is effective for oxidation of hardly oxidizable starting compounds, such as m-substituted compound, under a mild reaction condition using a relatively small amount of the catalyst (for example, in an amount not greater than 0.05 mol per mol of the starting compound).

According to the present invention, it has also been found that an improved result can be obtained by adding a co-oxidizer together with the bromine ion-supplying substance to the reaction system. The co-oxidizer in this case is defined as a substance capable of being oxidized easily under the reaction condition to form a peroxy radical R'-O-O- wherein R' stands for an organic residue. Illustrative of such co-oxidizer are, for example, aldehydes and ketones such as acetaldehyde, paraldehyde, cyclohexanone and methyl ethyl ketone as well as n-butene. Considering the effect, easiness in handling, price and compounds formed by oxidation of the co-oxidizer, advantageous are aldehydes and ketones, especially acetaldehyde, paraldehyde and methyl ethyl ketone. In the aspect of after-treatment of the reaction liquid, however, propionaldehyde is suitable when propionic acid is used as solvent while n-butyraldehyde is suitable when n-butyric acid is used as solvent. Thus, suitable co-oxidizers are not limited to the above mentioned three compounds.

The amount of the co-oxidizer is generally within the range of 0.0001~0.5 mol, preferably 0.001~0.2 mol per mol of the starting compound. If the amount is too small, the effect achieved by addition of the co-oxidizer will not be recognized. On the other hand, the use of an excess amount of the co-oxidizer will afford no particular influence on the oxidation reaction but is not preferable for an economical reason and for preventing any difficulty in control of the reaction as the amount of heat generated during the reaction may become larger by addition of a large amount of the co-oxidizer.

The effect achieved by addition of the co-oxidizer is similar to that achieved by addition of the bromine ion-supplying substance and effective for depression of the reaction temperature, shortening of the reaction time and increase in the rate of selection of the intermediate oxidation product aimed at. As in the case of adding the bromine ion-supplying substance, the effect achieved by adding the co-oxidizer becomes remarkable in the oxidation of hardly oxidizable compounds. In case easily oxidizable compounds such as p-methoxytoluene are oxidized at about 100° C., the beneficial effect is scarcely recognized. In case these compounds are oxidized at a temperature as low as room temperature, however, the effect achievable by adding the co-oxidizer can apparently be recognized. By taking the reactivity of compounds to be oxidized and the reaction conditions into consideration, therefore, it can easily be determined whether the co-oxidizer is jointly used with the bromine compound or not. In the case of oxidizing hardly oxidizable compounds, it is noted that depending on the reaction conditions adopted, the reaction would not proceed smoothly unless the co-oxidizer is jointly used with the bromine compound in the presence of a mixed solvent comprising a lower saturated fatty acid and an anhydride thereof. Accordingly, the conjoint use of the co-oxidizer with the bromine ion-supplying substance is generally advantageous, especially in the aspect of cost, for oxidation of hardly oxidizable compounds. In the present invention, the use of acetaldehyde, paraldehyde or methyl ethyl ketone as co-oxidizer gives an oxidation acetic acid as an oxidation product thereof. Similarly, the use of propionaldehyde or n-butyraldehyde gives on oxidation propionic acid or n-butyric acid, respectively. Consequently, a relatively large amount of such co-oxidizer permits the formation of a required amount of the lower saturated fatty acid at a relatively early stage of the oxidation even when the lower saturated fatty acid and/or an anhydride thereof is absent in the reaction system at the start of the reaction, and so serves to produce the desired intermediate oxidation product in a fairly good yield. This means that in the oxidation system for the starting compound it is possible to produce the lower saturated fatty acid in situ by previously using a large amount of the co-oxidizer. As is evident from Examples, this method is disadvantageous for an economical reason and is not preferable in that the rate of selection to the intermediate oxidation products is generally lower than the case of adding the lower saturated fatty acid and/or an anhydride thereof before or at the start of the reaction. In this method, addition of the co-oxidizer in an amount of 0.5~5 mols per mol of the starting compound is desirable but addition of such a large amount of the co-oxidizer will necessitate addition of an inert solvent as diluent for moderate control of the reaction and makes the optimum reaction condition relatively narrower.

The oxidation reactivity of the starting compounds used in the present invention varies significantly according to the bonding position of the ether linkage to the methyl group. Easiness in oxidation of the toluene derivatives can be expressed in the order of p>o>>m in terms of the position of the ether linkage to the methyl group. The p-substituted toluene is easily oxidizable only by the aid of a cobalt catalyst, thus minimizing the beneficial effect achieved by adding the bromine ion donor. On the other hand, the m-substituted toluene is very poor in reactivity in the case of using the cobalt catalyst alone, thus making the beneficial effect achieved by adding the bromine ion donor most remarkable.

Concerning the use of the solvent, acetic acid is advantageously used alone without being mixed with acetic anhydride if the cobalt salt is added in a fully sufficient amount. It has been found that the use of the lower saturated fatty acid jointly with an anhydride thereof in the oxidation reaction tends to form an ester of a substituted benzyl alcohol with the lower saturated fatty acid as compared with the case of using the lower saturated fatty acid alone as solvent. Considering the reaction conditions and the end product aimed at, it can conveniently be determined whether the lower saturated fatty acid is used alone or jointly with an anhydride thereof as solvent.

The optimum reaction temperature and oxygen pressure in practice of the present invention vary according to not only the sorts and quantities of the solvent, co-oxidizer and bromine ion-supplying substance and the like reaction conditions but also the sort of a compound to be oxidized and the difference in structure thereof. In general, however, the reaction temperature is within the range of 30°~200° C. and the oxygen pressure (or a partial pressure of oxygen) is within the range of 0.1~50 kg/cm² (absolute pressure). If the reaction temperature is too low, the reaction will not take place. On the other hand, if the reaction temperature is too high, the starting compound will be decomposed to form a hydroxy compound, thus inhibiting occurrence of the oxidation reaction. The range of the reaction temperature is more or less varied according to the oxygen pressure adopted. In the case of the oxidation reaction under pressurized oxygen, the reaction will start at a lower temperature as compared with the case of the reaction under normal pressure.

In order that the formation of carboxylic acids as by-products and the decomposition of the starting compounds can be inhibited to obtain the desired intermediate oxidation products such as alcohols and/or aldehydes in a good yield and at a high selectivity, it is important in the present invention to take care of the sort of the starting compounds and select concrete reaction conditions suitable for oxidizing the starting compounds.

In the present invention, the conversion rate which sometimes is referred to as reaction rate is generally limited lest it should exceed 90%. According to the process of this invention in which the oxidation conditions are devised so as to be very effective for the formation of intermediate oxidation products such as alcohols and aldehydes, the oxidation reaction may be carried out at a high conversion rate to obtain the desired products. If the conversion rate exceeds 90%, however, the amount of by-products formed will rapidly be increased to reduce the yield of the end product correspondingly. It is also important to adjust the optimum conversion rate according to the sort of the starting compound used. For example, in case a toluene having an ether group in its m-position is oxidized so as to obtain the desired intermediate oxidation product at a high rate of selection, the conversion rate is limited to 60% or less, preferably 15–50% as will be understood from the data shown in Examples. The minimum value of the conversion rate is generally limited to at least 10%, considering the economical aspect of the process. According to the sort of the end product or the commercial value of the end product, however, there is involved a case wherein the process is still economically attractive even at a lower conversion rate, for example, a conversion rate as low as 5–10%. Thus, the lower limit of the conversion rate is not limited to the above specified value. Unlike the case of oxidizing the starting compound having an ether group in its o- or p-position, the oxidation of the starting compound having an ether group in its m-position should be carried out at a conversion rate not greater than 60%. Otherwise, the desired intermediate oxidation product could not be obtained at a high rate of selection. This reason is not as yet made clear. However, this phenomenon is apparently observed irrespective of the sort of the ether group RO. In this respect, the case of oxidizing m-substituted toluene is significantly different form the case of oxidizing o- or p-substituted toluene. More precisely, the relation between the conversion rate and the rate of selection to the end product can be explained as follos: When methoxytoluenes were oxidized at conversion rates of 70%, 50%, 30% and 20% with an attempt to synthetize aldehydes, the rate of selection to aldehyde in the case of oxidizing the o-substituted toluene was 58, 62, 73 and 75, respectively, in terms of mol %, the rate of selection to aldehyde in the case of oxidizing the p-substituted toluene was 65, 63, 61 and 71, respectively, in terms of mol %, and the rate of selection to aldehyde in the case of oxidizing m-substituted toluene was only 16, 38, 70 and 67, respectively, in terms of mol %, thus showing that the rate of selection to aldehyde in the case of oxidizing the m-substituted toluene was rapidly decreased when the conversion rate exceeded 50%. A similar phenomenon was also observed when phenoxybenzaldehyde was obtained by oxidation of phenoxytoluene. In the case of oxidizing the o- and p-substituted toluene, the corresponding aldehydes could be obtained at a rate of selection of at least 50 mol % even at a conversion rate of 50–80% by selecting a proper reaction condition. In the case of oxidizing m-substituted toluene, for example, m-phenoxytoluene, however, it was difficult to increase the rate of selection to at least 40 mol %, irrespective of the reaction condition adopted, at a conversion rate of at least 50%. Especially, at a conversion rate of 60% or more, its was difficult to maintain the rate of selection at 25 mol %. Even in the event that the oxidation was carried out for the purpose of obtaining a mixture of an alcohol and an aldehyde, the relation between the conversion rate and the reate of selection showed the same tendency as in the above mentioned case. Hence, it was evident that when an ether group was present in m-position to methyl group of the starting compound, the desired intermediate oxidation product could not be obtained at a high rate of selection on condition that the conversion rate be kept at 60% or more. In the case of o- and p-substituted toluenes, it is also desirable to adjust the conversion rate properly to produce the desired intermediate oxidation product in a good yield. In the case of o-substituted compounds, for example, the conversion rate is desirably limited to at most 80%, preferably 15–75%. In the case of p-substituted compounds, the conversion rate is desirably limited to at most 90%, preferably 30–80%. When the starting compounds having two ether groups are oxidized, the conversion rate is also limited to at most 90%, preferably 20–85%.

When the reaction is carried out using m-substituted toluenes as starting compounds, the reaction temperature varies greatly according to whether the co-oxidizer is present or absent. In the absence of the co-oxidizer, the reaction temperature is within the range of 50°–180° C., preferably 60°–140° C., especially 110°–140° C. In the presence of the co-oxidizer, the reaction temperature is within the range of 30°–160° C., preferably 30°–80° C. The amount of the catalyst required for oxidizing the m-substituted toluenes is usually at least 0.01 mol per mol of the starting compounds. When the oxygen pressure becomes higher in the oxidation reaction, for example, when the partial pressure of oxygen is raised to at least 2 kg/cm$^2$, the minimum catalytically effective amount of the catalyst is decreased to 0.001 mol per mol of the starting compounds.

As the o- and p-substituted toluenes are more easily oxidized than the m-substituted toluenes, the reaction temperature may widely be varied but is usually within the range of 30°–180° C. The minimum catalytically effective amount of the catalyst in this case is at least 0.001 mol per mol of the starting compounds.

When the starting compounds having two ether groups are subjected to the oxidation reaction, the above mentioned tendency is also shown according to the relative positions of the ether groups to the methyl group. The reaction temperature adopted in this case is within the range of 40°–200° C. and the minimum catalytically effective amount of the catalyst is preferably at least 0.001 mol per mol of the starting materials.

According to the present invention, the starting compounds are oxidized at the methyl group bound to the benzene ring thereof to form the corresponding oxidized derivatives in which hydroxymethyl or formyl (aldehyde) group is present in place of the methyl group. In this case, the reaction conducted under a low oxygen pressure of 0.1~2 kg/cm² is clearly differentiated from the reaction conducted under a high oxygen pressure in the composition of the reaction liquid and in the optimum composition of the reaction liquid. In order to obtain the end product in a high yield, it is necessary to select properly the reaction conditions including the reaction temperature, the composition of the solvent, the amount of the catalyst and the like. Concerning the solvent, for instance, it is advantageous to use a mixed solvent comprising the lower satutated fatty acid and an anhydride thereof when an oxygen pressure as low as 0.1~2 kg/cm is used in the present invention. The use of such mixed solvent gives a high conversion rate and a high rate of selection to the end product. Concerning the catalyst, it is necessary to use it in an amount of at least 0.01 mol per mol of the starting compound to be oxidized. On the other hand, if the oxygen pressure is high, the reaction will proceed smoothly as compared with the case conducted under a low oxygen pressure. In this case, therefore, the limitation on the composition of solvent, the amount of catalyst and the like factors is less strict than the case of a low oxygen pressure.

By the term "molecular oxygen" used herein is meant, in addition to oxygen itself, various kinds of oxygen-containing gas such as air and a mixture of air and oxygen.

The mode of the oxidation reaction may be either of a batch operation and a continuous operation and can conveniently be determined by taking producibility, cost for facility and the like factors into consideration.

Separation and recovery of the end product, catalyst, solvent and starting material from the liquid reaction product can be carried out in a method known per se in this art for after-treatments. For example, the end product can be isolated easily and in a high yield from the liquid reaction product by removing the majority of the lower saturated fatty acid remaining in the reaction liquid by distillation under reduced pressure, adding toluene and water to the distillation residue, separating an aqueous phase having the catlyst and the lower saturated fatty acid dissolved therein from a toluene phase containing the starting material and the end product, and thereafter distilling the toluene phase under subatmospheric pressure. It is a matter of course that the solvent and the catalyst recovered in this manner can again be used for the reaction.

The present invention will now be illustrated in more detail by way of Examples. In the table shown in each Example, "Aldehyde", "Alcohol" and "Acetic ester" stand for those corresponding to the starting compound used.

EXAMPLE 1

In a 500 ml Pyrex glass 4-necked flask equipped with a stirrer, a thermometer, a gas inlet, a reflux condenser and a gas outlet was placed 200 ml of a liquid starting material mixture compound of m-phenoxytoluene, acetic acid, acetic anhydride, cobalt acetate tetrahydrate and a bromine compound in a proportion of 1:8:2:0.1:0.07 (in terms of molar ratio). The mixture was heated in an oil bath and the reaction temperature was maintained at a given value. An air stream was then introduced at a flow rate of 300 ml/min. into the mixture while stirring it vigorously at a rotation speed of 900–1000 rpm, and the mixture was reacted for 5 hours. The liquid reaction product was analyzed according to gas chromatography at elevated temperatures using as a filler silane-treated Celite 545 on which 10% by weight of Silicone oil OV-17 had been carried. The quantities of m-phenoxybenzaldehyde and m-phenoxybenzyl acetate formed were as shown in Table 1. When a bromine compound was not added, the reaction did not take place under the same condition. m-Phenoxybenzyl alcohol was not formed in all of the experiments shown in Table 1.

The starting m-phenoxytoluene was synthetized by adding 1.0 mol of bromobenzene, 1.0 mol of potassium hydroxide and 1 g of copper powder to 1.25 mols of m-cresol, heating the mixture under agitation while expelling the formed water out of the reaction system, and reacting the mixture for 60 minutes after the reaction temperature reached 200° C. The crude starting material was completely purified before use by extracting it with benzene and then repeating a washing treatment with alkali and distillation.

TABLE 1

| Exp. No. | Bromine Compound | Reaction temperature (°C.) | Conversion rate (%) | Rate of selection (mol %) | |
|---|---|---|---|---|---|
| | | | | Aldehyde | Acetic ester |
| 1 | Br₂*¹ | 112–114 | 45 | 19 | 6 |
| 2 | HBr*² | 117–119 | 31 | 9 | 41 |
| 3 | LiBr . H₂O | 119–120 | 41 | 16 | 46 |
| 4 | NaBr*³ | 108–111 | 42 | 48 | 2 |
| 5 | KBr | 120–121 | 21 | 12 | 57 |
| 6 | MgBr₂ . 6H₂O | 118–119 | 25 | 9 | 51 |
| 7 | AlBr₃ . 6H₂O | 107–113 | 17 | 6 | 48 |
| 8 | CoBr₂ . 6H₂O | 101–103 | 23 | 14 | 49 |
| 9 | n-C₃H₇Br*⁴ | 109–112 | 15 | 45 | 7 |
| 10 | Bromobenzene*⁵ | 119–120 | 6 | 20 | 24 |
| 11 | NH₄Br | 102–105 | 28 | 15 | 43 |
| 12 | FeBr₃ | 115–119 | 32 | 11 | 47 |
| 13 | CuBr₂ | 108–112 | 27 | 12 | 39 |
| 14 | CH₃COBr | 112–117 | 34 | 10 | 44 |

Remarks:
*¹The composition of the liquid starting material mixture was as follows: Starting material: acetic acid:Br₂:Co = 1:7:0.02:0.1 (in terms of molar ratio). The bromine (Br₂) was partly converted in the reaction system easily into an organobromine compound and HBr.
*²A commercial available reagent of special grade (purity: 47–48% as aqueous solution) was used as such.
*³The composition of the liquid starting material mixture was as follows: Starting material:acetic acid:NaBr:Co = 1:8:0.01:0.1 (molar ratio) The oxidation with oxygen was conducted for one hour (free rate: 3.6 liters/hr).
*⁴Oxygen was used as oxidizing agent (feed rate: 3.6 liters/hr) and the reaction time was one hour.
*⁵The composition of the liquid starting material mixture was as follows: Starting material:acetic acid:acetic anhydride:Br:Co = 1:7:3:0.2:0.2 (molar ratio). The reaction time was 6 hours.

EXAMPLE 2

Using cobalt acetate as cobalt salt, lithium bromide (sodium bromide in the experiments with a white asterisk) as bromine compound and a mixture of acetic acid and acetic anhydride as solvent, the oxidation treatment of m-phenoxytoluene under normal pressure was carried out under various reaction conditions. The results obtained are shown in Table 2. The method for experiments and the method for analysis of the product were quite identical with those described in Example 1.

TABLE 2

| Exp. No. | Molar ratio to starting material | | | | Reaction temperature (°C.) | Reaction time (hr) | Conversion rate (%) | Rate of selection (mol %) | | |
|---|---|---|---|---|---|---|---|---|---|---|
| | AcOH | Ac₂O | Co | Br | | | | Aldehyde | Alcohol | Acetic ester |
| 1 | 2 | 0 | 0.1 | 0.1 | 115–116 | 5 | 9 | 15 | — | 10 |
| 2 | 5 | 0 | 0.1 | 0.1 | 111–112 | 5 | 16 | 38 | — | 20 |
| 3 | 5*¹ | 0 | 0.1 | 0.01ᴼ | 123–130 | 1 | 46 | 28 | 0 | 3*⁶ |
| 4 | 6 | 1 | 0.1 | 0.01 | 111–113 | 5 | 26 | 26 | — | 35 |
| 5 | 6 | 1 | 0.1 | 0.0005 | 114–115 | 4 | 12 | 38 | — | 31 |
| 6 | 6 | 1 | 0.01 | 0.05 | 114–116 | 5 | 12 | 25 | — | 28 |
| 7 | 6 | 1 | 0.01*² | 0.1 | 111–112 | 5 | 12 | 18 | — | 20 |
| 8 | 7 | 2 | 0.1 | 0.07 | 65–76 | 4 | 28 | 39 | — | 20 |
| 9 | 7 | 0 | 0.1 | 0.03 | 68–75 | 2*³ | 39 | 41 | 0 | 0 |
| 10 | 8 | 2 | 0.1 | 0.01ᴼ | 60–64 | 1 | 21 | 58 | 4.0 | 6 |
| 11 | 8 | 1 | 0.1 | 0.2 | 113–115 | 5 | 52 | 17 | 0.7 | 24 |
| 12 | 8 | 1 | 0.1 | 0.5 | 113–115 | 5 | 37 | 18 | 0.2 | 25 |
| 13 | 8 | 0 | 0.1 | 0.01ᴼ | 108–111 | 1 | 42 | 48 | 2.0 | 2.0 |
| 14 | 8 | 0 | 0.1 | 0.01ᴼ | 60–62 | 2 | 41 | 36 | trace | trace |
| 15 | 8 | 0 | 0.05 | 0.01ᴼ | 70–71 | 3 | 9 | 39 | 1.7 | 3.5 |
| 16 | 10 | 0 | 0.1 | 0.1 | 112–115 | ⅓*³ | 21 | 64 | 2.0 | 9 |
| 17 | 10 | 0 | 0.2*⁴ | 0.2 | 111–113 | 5 | 26 | 45 | — | 20 |
| 18 | 10 | 0 | 0.2*⁵ | 0.01ᴼ | 65–68 | 2 | 38 | 41 | 1.5 | 2.0 |
| 19 | 10 | 0 | 0.3 | 0.1 | 111–113 | 5 | 21 | 40 | — | 22 |
| 20 | 15 | 0 | 0.1 | 0.1 | 110–113 | 5 | 27 | 40 | — | 17 |
| 21 | 8 | 0 | 0.1*⁷ | 0 | 112–114 | 1 | 41 | 33 | 11 | 6.3 |
| 22 | 10 | 0 | 0.2*⁸ | 0.01ᴼ | 94–96 | 1 | 33 | 42 | 0 | trace |
| 23 | 8 | 0 | 0.1 | 0.01ᴼ | 108–110 | 7/3 | 90 | 3.7 | 0.2 | 0.1 |
| 24 | 10 | 1 | 0.2 | 0.02 | 110–113 | 8 | 68 | 8.5 | 0.5 | 9 |
| 25 | 8 | 2 | 0.1 | 0.01ᴼ | 50–51 | 4 | 0 | — | — | — |
| 26 | 0.5 | 0 | 0.2*⁴ | 0.01 | 100–105 | 8 | 3 | 5.0 | 0.1 | 4.0 |

Remarks:
Oxygen was used as oxidizing agent in the experiments marked with ᴼ (feed rate: 3.6 liters/hr) while air was used as oxidizing agent in the other experiments (feed rate: 300 ml/min).
*¹Propionic acid was used in place of acetic acid.
*²Cobalt (bivalent) acetylacetanate was used in place of cobalt acetate tetrahydrate.
*³Oxygen (3.6 liters/hr) was used oxidizing agent in place of air.
*⁴Cobalt benzoate was used in place of cobalt acetate tetrahydrate.
*⁵Cobalt stearate was used in place of cobalt acetate tetrahydrate.
*⁶Propionate
*⁷Cobalt bromide hexahydrate was used in place of cobalt acetate tetrahydrate and sodium acetate in 0.2 molar proportion to the starting material was added. When cobalt bromide and sodium acetate were added, cobalt acetate and sodium bromide were easily formed in the reaction system and so the same effect as in the case of adding cobalt acetate and sodium bromide was obained.
*⁸Cobalt hydroxide (60% by weight in cobalt content) was used cobalt acetate tetrahydrate.
*⁹Experiments Nos. 23–26 stand for Comparative Examples.

EXAMPLE 3

Except that m-methoxytoluene was used as starting material to be oxidized, the experiments were carried out in the same manner as described in Example 2 whereby the results shown in Table 3 were obtained. In these experiments NaBr was used as bromine compound and oxygen (feed rate: 3.0–3.6 liters/hr) was used as oxidizing agent. The m-methoxytoluene was synthetized by methylating m-cresol with dimethyl sulfate in a usual manner and completely purified in the same manner as described in Example 1 before use. In Table 3, Experiments Nos. 15–20 stand for Comparative Examples.

TABLE 3

| Exp. No. | Molar ratio to starting material | | | | Reaction temperature (°C.) | Reaction time (hr). | Conversion rate (%) | Rate of selection (mol %) | | |
|---|---|---|---|---|---|---|---|---|---|---|
| | AcOH | Ac₂O | Co | Br | | | | Aldehyde | Alcohol | Acetic ester |
| 1 | 0 | 8 | 0.1 | 0.01 | 112–116 | 1.0 | 12 | 8 | 0.5 | 10.5 |
| 2 | 1 | 0 | 0.04 | 0.01 | 68–74 | 1.0 | 28 | 20 | 0.4 | 0 |
| 3 | 2 | 0 | 0.07 | 0.005 | 111–112 | 1.0 | 34 | 36 | 0.2 | 0 |
| 4 | 4 | 3 | 0.05*¹ | 0.05 | 74–76 | 3.0 | 48 | 24 | 0.2 | 2.5 |
| 5 | 5 | 0 | 0.1*² | 0.001 | 80–85 | 1.5 | 21 | 44 | 0.1 | 0.3 |
| 6 | 5 | 3 | 0.1 | 0.1 | 110–112 | 1.5 | 39 | 42 | 0.4 | 5.7 |
| 7 | 8 | 0 | 0.1 | 0.01 | 60–65 | 7.0 | 56 | 35 | 1.0 | trace |
| 8 | 8 | 0 | 0.1 | 0.01 | 60–65 | 1.5 | 23 | 59 | 1.7 | trace |
| 9 | 8 | 2 | 0.2 | 0.0002 | 80–83 | 1.5 | 25 | 29 | 0.5 | 3.5 |
| 10 | 8 | 2 | 0.1 | 0.05*³ | 118–121 | 6.0*⁴ | 41 | 8 | — | 42 |
| 11 | 10 | 2 | 0.05 | 0.4 | 95–97 | 1.5 | 42 | 31 | 0.1 | 2.2 |
| 12 | 10*⁵ | 0 | 0.3 | 0.005 | 100–104 | 1.5 | 34 | 48 | 3.2 | 0.1*⁷ |
| 13 | 8 | 0 | 0.1*⁸ | 0.01 | 111–114 | 1.0 | 33 | 57 | 0.1 | 0.3 |
| 14 | 8 | 0 | 0.1*⁹ | 0.05 | 85–88 | 1.5 | 21 | 58 | 1.1 | trace |
| 15 | 8 | 2 | 0.1 | 0 | 118–120 | 6.0*⁴ | 0 | — | — | — |
| 16 | 8 | 0 | 0.1 | 0 | 60–108 | 4.0 | 8 | 9 | 0 | 4.0 |
| 17 | 8 | 0 | 0.1 | 0.01 | 50–52 | 4.0 | 0 | — | — | — |
| 18 | 8 | 0 | 0.01 | 0.01 | 60–64 | 3.0 | 2 | 0 | 0 | 0 |
| 19 | 0 | 0 | 0.05*⁶ | 0.01 | 130–135 | 6.0 | 4 | 0 | 0 | 0 |

TABLE 3-continued

| Exp. No. | Molar ratio to starting material | | | | Reaction temperature (°C.) | Reaction time (hr). | Conversion rate (%) | Rate of selection (mol %) | | |
|---|---|---|---|---|---|---|---|---|---|---|
| | AcOH | Ac$_2$O | Co | Br | | | | Aldehyde | Alcohol | Acetic ester |
| 20 | 8 | 0 | 0.2 | 0.02 | 110-112 | 4.0 | 72 | 11 | 0.5 | 6.5 |

Remarks:
*[1]Cobalt nitrate hexahydrate was used in place of cobalt acetate tetrahydrate.
*[2]Cobalt naphthenate (10% by weight in cobalt content) was used in place of cobalt acetate tetrahydrate.
*[3]KBr was used in place of NaBr.
*[4]Air (flow rate: 300 ml/min.) was used as oxidizing agent.
*[5]n-Butyric acid was used in place of acetic acid.
*[6]Cobalt (bivalent) acetylacetonate was used in place of cobalt acetate tetrahydrate.
*[7]n-Butyrate
*[8]In addition to cobalt acetate tetrahydrate, 0.01 molar proportion of nickel acetate tetrahydrate and 0.005 molar proportion of cerium acetate monohydrate based on the starting material were added. When very small amounts of Ni ions and Ce ions were allowed to be present together with Co ions as seen in this experiment, the result of the reaction was sometimes better but the rate was not so great and was only equivalent to the best result obtained in the case of using cobalt alone.
*[9]In addition to cobalt tetrahydrate, 0.03 molar proportion of manganese acetate based on the starting material was added. In this case, the result of the reaction was slightly better as in the case of *8. A slightly better result to such degree was also seen in the case of adding a very small amount of Cr ions.

EXAMPLE 4

In the same manner as described in Example 3, various compounds were oxidized with oxygen. When comparison was made between the case wherein a bromine compound was present in the reaction system and the case wherein such bromine compound was absent in the reaction system, it was found that in the case wherein the bromine compound was absent, no reaction took place under the reaction conditions shown in Table 4. The results of experiments where the reaction took place were as shown in Table 4.

and a gas outlet was placed 200 ml of the liquid starting material mixture composed of m-phenoxytoluene, acetic acid, paraldehyde, cobalt acetate tetrahydrate and a bromine compound in a proportion of 1:12.5:0.03:0.3:0.04 (molar ratio). The mixture was maintained in a water bath a reaction temperature of 50°-55° C. and an air stream was then introduced at a flow rate of 300 ml/min. into the mixture while stirring it vigorously at a rotation speed of 1000-1200 rpm. The reaction was conducted for a given period of time and the product was analyzed in the same manner as described in Example 1. The results of experiments were

TABLE 4

| Exp. No. | R in Starting*[1] material | Molar ratio*[2] | | | Bromine compound*[2] (mol ratio) | | Reaction temperature (°C.) | Reaction time (hr) | Conversion rate (%) | Rate of selection (mol %) | | |
|---|---|---|---|---|---|---|---|---|---|---|---|---|
| | | AcOH | Ac$_2$O | CO | | | | | | Aldehyde | Alcohol | Acetic ester |
| 1 | n-C$_4$H$_9$ | 8 | 2 | 0.1 | LiBr . H$_2$O | (0.05) | 114-113 | 3 | 34 | 14 | — | 39 |
| 2 | n-C$_8$H$_{17}$ | 10 | 3 | 0.1 | NaBr | (0.05) | 117-120 | 3 | 41 | 15 | — | 35 |
| 3 | Cyclohexyl | 10 | 3 | 0.1 | KBr | (0.06) | 115-116 | 5*[4] | 10 | 14 | — | 23 |
| 4 | m-tolyl | 8 | 2 | 0.1 | NaBr | (0.04) | 117-118 | 4*[4] | 47 | 11 | — | 23 |
| 5 | n-C$_{12}$H$_{25}$ | 10*[3] | 0 | 0.1 | NaBr | (0.05) | 170-176 | 0.2*[5] | 24 | 11 | 1.1 | 3.5*[6] |
| 6 | n-C$_8$H$_{17}$ | 10*[3] | 0 | 0.1 | NaBr | (0.05) | 150-154 | 0.2*[5] | 34 | 42 | 0.3 | 0.3*[6] |

Remarks:
*[1]The starting compounds were shown by the general formula

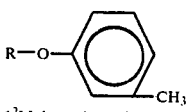

*[2]Molar ratio to the starting compounds
*[3]n-Butyric acid was used in place of acetic acid.
*[4]Air (flow rate: 300 ml/min.) was used as oxidizing agent in place of oxygen.
*[5]The experiment was carried out by using a 400 ml SUS-316 stainless steel autoclave equipped with a stirrer, a thermometer and a gas inlet and oxidizing the starting material with oxygen under a pressure of 1.5 kg/cm$^2$ (absolute). In this case, the oxygen was supplied from a pressure tank through a pressure regulator and the oxygen pressure was maintained at all times at 1.5 kg/cm$^2$. The stirring velocity was 1600 rpm.
*[6]n-Butyrate

EXAMPLE 5

In a 500 ml Pyrex glass 4-necked flash equipped with a stirrer, a thermometer, a gas inlet, a reflux condenser as shown in Table 5. In case the co-oxidizer was not added, the mixture was not at all reacted even when the bromine compound was added.

TABLE 5

| Exp. No. | Bromine compound | Reaction time (hr) | Conversion rate (%) | Rate of selection (mol %) | | | |
|---|---|---|---|---|---|---|---|
| | | | | Aldehyde | Alcohol | Acetic ester | Acid |
| 1 | HBr*[4] | 3 | 39 | 53 | 3 | 0.1 | — |
| 2 | Br$_2$ | 2 | 24 | 44 | 0 | 0.9 | — |
| 3 | LiBr . H$_2$O | 2 | 21 | 87 | 0.3 | 0.2 | — |
| 4 | NaBr | 1 | 11 | 71 | 10.0 | 0 | — |
| 5 | NaBr | 2 | 22 | 74 | 2.3 | 0 | 14 |
| 6 | NaBr*[1] | 2 | 27 | 61 | 2.5 | 0.4 | — |
| 7 | NaBr | 3 | 45 | 60 | 0.4 | 0.2 | 35 |

TABLE 5-continued

| Exp. No. | Bromine compound | Reaction time (hr) | Conversion rate (%) | Rate of selection (mol %) | | | |
|---|---|---|---|---|---|---|---|
| | | | | Aldehyde | Alcohol | Acetic ester | Acid |
| 8 | KBr*2 | 1 | 35 | 62 | 0.1 | 0.4 | — |
| 9 | NaBr + LiBr . H2O*3 | 2 | 14 | 76 | 5.0 | 0.3 | — |
| 10 | MgBr2 . 6H2O*2 | 1 | 37 | 48 | 1.3 | 0.1 | — |
| 11 | AlBr3 . 6H2O*2 | 1 | 28 | 57 | 0.5 | 1.3 | — |
| 12 | CoBr2. 6H2O | 2 | 19 | 71 | 5.0 | 0.7 | — |
| 13 | Ethyl bromide | 1 | 7 | 63 | 0 | 0.4 | — |
| 14 | Bromobenzene*2 | 1.5 | 15 | 20 | 0.3 | 1.1 | — |
| 15 | NH4Br | 1.5 | 29 | 55 | 1.3 | 0.2 | — |
| 16 | FeBr3 | 2 | 32 | 49 | 1.7 | 0.5 | — |
| 17 | CuBr2 | 2 | 25 | 57 | 0.7 | 0.2 | — |
| 18 | CH3COBr | 2 | 21 | 42 | 0.4 | 0.1 | — |

Remarks:
*1In this experiement, NaBr and paraldehyde were added in amounts of 0.1 mol and 0.2 mol, respectively, per mol of the starting material.
*2Oxygen (flow rate: 3.6 liters/hr) was used as oxidizing agent in place of air.
*3Added respectively in 0.02 molar proportion to m-phenoxytoluene

EXAMPLE 6

Using NaBr as bromine compound, the oxidation experiment was carried out in the same manner as described in Example 5 to study the relation between the reaction temperature and the results of reaction. The results of the experiments are shown in Table 6.

TABLE 6

| Exp. No. | Reaction temperature (°C.) | Reaction time (min.) | Conversion rate (%) | Rate of selection (mol %) | | | |
|---|---|---|---|---|---|---|---|
| | | | | Aldehyde | Alcohol | Acetic ester | Acid |
| 1*1 | 28–32 | 80 | 9 | 56 | 0 | 6.1 | — |
| 2*2 | 31–34 | 240 | 11 | 19 | 2.0 | 0.5 | — |
| 3 | 39.5–40.5 | 120 | 14 | 75 | 1.0 | 0 | — |
| 4 | 52.0–54.5 | 120 | 22 | 71 | 3.5 | 0 | 14.2 |
| 5 | 79.8–83.0 | 120 | 32 | 40 | 3.4 | 1.3 | — |
| 6 | 104–106 | 120 | 16 | 25 | 3.2 | 5.4 | — |
| 7*3 | 109–110 | 300 | 47 | 32 | 0 | 8 | — |
| 8*4 | 108–114 | 300 | 49 | 25 | 0 | 43 | — |
| Referential Example | | | | | | | |
| 9 | 155–260 | 120 | 0 | — | — | — | — |

Remarks:
*1The composition of the reaction liquid was as follows: m-phenoxytoluene:acetic acid:cobalt acetate tetrahydrate:NaBr:acetaldehyde = 1:8:0.05:0.01:0.03 (molar ratio). Oxygen (flow rate: 3.6 liters/hr) was used as oxidizer.
*2The composition of the reaction liquid was as follows: m-phenoxytoluene:acetic acid:cobalt acetate tetrahydrate:NaBr:acetaldehyde = 1:8:0.01:0.01:0.03 (molar ratio) Oxygen (flow rate: 3.6 liters/hr) was used as oxidizing agent.
*3The composition of the reaction liquid was as follows: m-phenoxytoluene:acetic acid:acetic anhydride:cobalt acetate tetrahydrate:LiBr H2O:paraldehyde = 1:7:0.5:0.1:0.07:0.03 (molar ratio)
*4The composition of the reaction liquid was as follows: m-phenoxytoluene:acetic acid:acetic anhydride:cobalt acetate tetrahydrate:LiBr H2O:acetaldehyde = 1;7;1;0.1;0.07;0.1 (molar ratio)

EXAMPLE 7

Using cobalt acetate tetrahydrate as catalyst, acetic acid as solvent, NaBr as bromine compound and acetaldehyde as co-oxidizer, the oxidation treatment of m-methoxytoluene under normal pressure was carried out under various reaction conditions. The results obtained are shown in Table 7. The reaction apparatus and the method for analysis of the product were quite identical with those described in Example 5. The m-methoxytoluene used as starting material was synthetized according to a usual method by reacting m-cresol with dimethyl sulfate and was sufficiently purified before use.

TABLE 7

| Exp. No. | Molar ratio to m-methoxytoluene | | | | Reaction temperature (°C.) | Reaction time (min.) | Conversion rate (%) | Rate of selection (mol %) | | |
|---|---|---|---|---|---|---|---|---|---|---|
| | AcOH | Co | NaBr | AcH | | | | Aldehyde | Alcohol | Acetic ester |
| 1 | 15 | 0.2 | 0.05 | 0.05*1 | 60–62 | 30 | 30 | 55 | 14.0 | 0 |
| 2 | 10 | 0.2*2 | 0.1 | 0.05*3 | 80–83 | 30 | 19 | 53 | 3.0 | 2 |
| 3 | 8 | 0.1 | 0.01 | 0.03 | 38–40 | 70 | 58 | 21 | 0.7 | trace |
| 4 | 8 | 0.1 | 0.01 | 0.03 | 45–48 | 60 | 40 | 55 | 0.8 | trace |
| 5 | 8 | 0.1 | 0.01 | 0.03 | 32–34 | 180 | 15 | 64 | 3.6 | 1.1 |
| 6 | 8 | 0.01 | 0.01 | 0.03 | 58–62 | 180 | 4 | 18 | 13.4 | 0 |
| 7 | 8 | 0.1 | 0.01 | 0.005*3 | 62–66 | 90 | 21 | 65 | 2.0 | 0 |
| 8 | 8 | 0.1 | 0.01 | 0.03*3 | 108–114 | 20 | 46 | 49 | 1.0 | 6.0 |
| 9 | 8 | 0.1 | 0.0001 | 0.03 | 60–65 | 90 | 8 | 30 | 5.0 | 0 |
| 10 | 5 | 0.1*4 | 0.03 | 0.1 | 42–44 | 90 | 18 | 49 | 0 | 0 |
| 11 | 5*5 | 0.05 | 0.01 | 0.03 | 68–71 | 150 | 16 | 19 | 2.3 | 9.5 |
| 12 | 5 | 0.15 | 0.01 | 0.001*3 | 64–67 | 90 | 20 | 60 | 0.3 | 0.1 |
| 13 | 2 | 0.05 | 0.01*6 | 0.1 | 66–70 | 25 | 27 | 67 | 1.0 | 0 |

TABLE 7-continued

| Exp. No. | Molar ratio to m-methoxytoluene | | | | Reaction temperature (°C.) | Reaction time (min.) | Conversion rate (%) | Rate of selection (mol %) | | |
|---|---|---|---|---|---|---|---|---|---|---|
| | AcOH | Co | NaBr | AcH | | | | Aldehyde | Alcohol | Acetic ester |
| 14 | 2 | 0.1*[2] | 0.01 | 0.0003*[3] | 70–73 | 30 | 16 | 45 | 1.1 | 0.3 |
| 15 | 1 | 0.03 | 0.01 | 0.1*[3] | 64–68 | 30 | 18 | 39 | 1.3 | 0 |
| 16 | 0.5 | 0.03*[7] | 0.01 | 0.1*[3] | 65–71 | 30 | 16 | 18 | 0.6 | 0 |
| 17 | 0.3 | 0.02*[8] | 0.01 | 0.3*[3] | 72–75 | 60 | 27 | 14 | 1.2 | 0 |
| (Referential Examples) | | | | | | | | | | |
| 18 | 5 | 0.005 | 0.005 | 0.1 | 70–72 | 180 | 0 | — | — | — |
| 19 | 8 | 0.1 | 0.01 | 0.03 | 68–72 | 180 | 71 | 9 | 1.0 | — |
| 20 | 0 | 0.03*[8] | 0.03 | 0.3*[3] | 71–74 | 420 | 13 | 3 | 0 | 0 |
| 21 | 8 | 0.1 | 0 | 0 | 60–108 | 240 | 8 | 9 | 0 | 4.0 |
| 22 | 8 | 0.1*[9] | 0.01 | 0.03*[3] | 60–62 | 90 | 29 | 75 | trace | 0 |
| 23 | 8 | 0.1*[10] | 0.01 | 0.03*[3] | 60–63 | 90 | 27 | 69 | 0.1 | 1.7 |

Remarks:
*[1]Methyl ethyl ketone used in place of AcH (acetaldehyde).
*[2]Cobalt benzoate was used in place of cobalt acetate tetrahydrate.
*[3]Paraldehyde was used in place of AcH.
*[4]Cobalt naphthenate (10% by weight in cobalt content) was used in place of cobalt acetate tetrahydrate.
*[5]Acetic anhydride was used in place of AcOH.
*[6]KBr was used in place of NaBr.
*[7]About one third of the quantity of cobalt acetate tetrahydrate added was insoluble in the reaction liquid at the reaction temperature.
*[8]In these experiments a part of cobalt acetate tetrahydrate was insoluble in the reaction liquid at the start of the reaction but was almost completely dissolved in the reaction liquid on completion of the reaction probably due to the reaction that acetic acid was formed by oxidation of the co-oxidizer.
*[9]In addition to cobalt acetate tetrahydrate, 0.01 molar proportion of nickel acetate tetrahydrate based on the starting m-methoxytoluene was added. This experiment obviously shows that when a very small amount of Ni ions is allowed to be co-existent with Co ions, the result is sometimes better but the rate is not so great and is only equivalent to the best result obtained in the case of using Co salt alone under the optimum conditions (the result of Exp. No. 3 in Table 5 referred to). Only a very poor result is obtained by adding Ni ions alone. This fact obviously shows that the main catalytic effect is achieved by the active seed formed by the Co - Br system.
*[10]In addition to cobalt acetate tetrahydrate, 0.01 molar proportion of nickel acetate tetrahydrate and 0.005 molar proportion of cerium monohydrate based on the starting m-methoxytoluene were added. In this experiment, the result seems to be somewhat better. An improvement in the result to such degree was achieved also in the case of adding a very small amount of Cr ions of Mn ions.

EXAMPLE 8

Except that the starting material to be oxidized was m-phenoxytoluene, the experiment was carried out in the same manner as illustrated in Example 7 whereupon the results as shown in Table 8 were obtained.

the reaction system, the reaction did not take place under the reaction conditions shown in Table 9 and still failed to take place within 3 hours even in the case of elevating the reaction temperature to about the boiling point of acetic acid and using as solvent a mixture of 2–3 molar proportion of acetic anhydride and 8–10 molar

TABLE 8

| Exp. No. | Molar ratio to m-phenoxytoluene | | | | Reaction temperature (°C.) | Reaction time (min.) | Conversion rate (%) | Rate of selection (mol %) | | | |
|---|---|---|---|---|---|---|---|---|---|---|---|
| | AcOH | Co | NaBr | AcH | | | | Aldehyde | Alcohol | Acetic ester | Acid |
| 1 | 20 | 0.3 | 0.001 | 0.03 | 40–42 | 60 | 34 | 40 | 0.3 | 0 | — |
| 2 | 10 | 0.1 | 0.1 | 0.3*[1] | 105–110 | 300 | 40 | 32 | 1.6 | 8.9 | 28 |
| 3 | 10 | 0.05*[2] | 0.5 | 0.1 | 50–54 | 300 | 27 | 28 | 0 | 0.8 | — |
| 4 | 8*[3] | 0.1 | 0.01 | 0.03*[1] | 100–101 | 30 | 57 | 35 | 2.0 | 0.1*[8] | — |
| 5 | 8 | 0.1*[4] | 0.01 | 0.03 | 58–60 | 30 | 8 | 31 | 1.0 | 0.3 | — |
| 6 | 8 | 0.1*[5] | 0.01 | 0.03 | 64–66 | 40 | 17 | 55 | 1.0 | 0 | — |
| 7 | 2 | 0.05 | 0.01*[6] | 0.1*[7] | 70–74 | 40 | 23 | 42 | 9.0 | 0 | — |
| 8 | 1 | 0.05*[5] | 0.05 | 0.1 | 55–57 | 30 | 17 | 31 | 0.7 | 0 | — |
| 9 | 10 | 0.1*[9] | 0.01 | 0.1*[1] | 112–114 | 150 | 45 | 48 | trace | 2 | — |
| 10 | 8 | 0.1*[10] | 0 | 0.05*[1] | 108–113 | 120 | 33 | 51 | 0.5 | 0.3 | — |
| (Referential Examples) | | | | | | | | | | | |
| 11 | 5 | 0.003 | 0.001 | 0.03*[1] | 100–105 | 240 | 0 | — | — | — | — |
| 12 | 8 | 0.1 | 0.01 | 0.03 | 64–68 | 180 | 69 | 8 | 1.0 | 0 | — |

Remarks:
*[1]Paraldehyde was used in place of AcH and air was used as oxidizing agent.
*[2]Cobalt stearate was used in place of cobalt acetate tetrahydrate.
*[3]Propionic acid was used in place of acetic acid.
*[4]Cobalt nitrate hexahydrate was used in place of cobalt acetate tetrahydrate.
*[5]Cobalt (bivalent) acetylacetonate was used in place of cobalt acetate tetrahydrate.
*[6]KBr was used in place of NaBr.
*[7]Methyl ethyl ketone was used in place of AcH.
*[8]Propionate
*[9]Cobalt hydroxide (60% by weight in cobalt content) was used inplace of cobalt acetate tetrahydrate.
*[10]Cobalt bromide hexahydrate was used in place of cobalt acetate tetrahydrate and 0.2 molar proportion of sodium acetate based on the starting m-phenoxytoluene was used. When cobalt bromide was added together with sodium acetate as seen in this experiment, these compounds were supposed to be converted easily into cobalt acetate and sodium bromide whereby the same effect as obtained in the case of adding cobalt acetate tetrahydrate and sodium bromide was obtained.

EXAMPLE 9

The oxidation experiment of various compounds with oxygen was carried out in the same manner as described in Example 5 to compare the case of allowing a bromine compound and a co-oxidizer to be present in the reaction system with the case of not allowing these ingredients to be present in the reaction system. In case the bromine compound and the co-oxidizer were absent in proportion of acetic acid based on the starting compound. The results of experiments obtained in the case of allowing the co-oxidizer and the bromine compound to be present in the reaction system are shown in Table 9. The starting compound was synthetized in a usual manner from m-cresol and a bromohydrocarbon. The reaction product was identified by the GC-MS method.

TABLE 9

| Exp. No. | R in starting material*1 | Molar ratio*2 AcOH | Molar ratio*2 Co | Bromine compound | (molar ratio)*2 | Co-oxidizer | (molar ratio)*2 | Reaction temperature (°C.) | Reaction time (min.) | Conversion rate (%) | Rate of selection (mol %) Aldehyde | Alcohol | Ester |
|---|---|---|---|---|---|---|---|---|---|---|---|---|---|
| 1 | n-C4H9 | 10 | 0.1 | LiBr . H2O | (0.05) | PA*3 | (0.03) | 70–74 | 120 | 18 | 42 | 0.5 | 0.1 |
| 2 | n-C3H7 | 8 | 0.1 | NaBr | (0.01) | AcH | (0.03) | 67–68 | 350 | 37 | 23 | 4.0 | 8.0 |
| 3 | Cyclohexyl | 15 | 0.1 | KBr | (0.03) | MEK*4 | (0.03) | 60–62 | 120 | 15 | 34 | 1.0 | 3.0 |
| 4 | m-Mcφ | 15 | 0.1 | NaBr | (0.01) | AcH | (0.03) | 58–61 | 90 | 33 | 60 | 2.0 | 2.0 |
| 5 | n-C12H25*6 | 10*5 | 0.2 | KBr | (0.03) | MEK*4 | (0.05) | 154–156 | 30 | 14 | 21 | 0 | 0 |
| 6 | n-C6H13*6 | 10 | 0.1 | NaBr | (0.03) | MEK*4 | (0.03) | 100–109 | 40 | 38 | 24 | 0 | 1.5 |

Remarks:

*1 The starting compounds are shown by the general formula

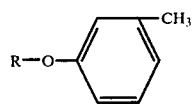

*2 Molar ratio to the starting compound
*3 Paraldehyde
*4 Methyl ethyl ketone
*5 n-Butyric acid was used in this experiment in place of acetic acid.
*6 In this experiment, the oxidation of the starting compound with oxygen was conducted at an oxygen pressure of 1.5 kg/cm² (absolute pressure) using a 400 ml SUS-316 stainless steel autoclave equipped with a stirrer, a thermometer and a gas inlet. In this case, the oxygen was supplied from a pressure tank through a pressure regulator and the oxygen pressure was maintained at all times at 1.5 kg/cm². The stirring velocity was 1600 rpm.

EXAMPLE 10

In a 500 ml Pyrex glass 4-necked flask equipped with a stirrer, a thermometer, a gas inlet, a reflux condenser and a gas outlet was placed 200 ml of a liquid starting material mixture composed of o-methoxytoluene, acetic acid, cobalt acetate tetrahydrate and a bromine compound in a proportion of 1:8:0.1:0.01 (molar ratio). The mixture was maintained in a water bath at a reaction temperature of 60°–65° C. and an oxygen stream was introduced at a flow rate of 3.6 liters/hr into the mixture while stirring it vigorously at a rotation speed of 1000 rpm. The reaction was conducted at a given period of time. The reaction product was analyzed in the same manner as described in Example 1. The results of experiments are shown in Table 10. When the bromine compound was not added, the reaction did not take place under the above condition. The starting o-methoxytoluene was synthetized according to a usual method by reacting o-cresol with dimethyl sulfate and sufficiently purified before use by repeating washing with alkali and distillation.

TABLE 10

| Exp. No. | Bromine compounds | Reaction time (min.) | Conversion rate (%) | Rate of selection (mol %) Aldehyde | Alcohol | Acetic ester |
|---|---|---|---|---|---|---|
| 1 | KBr | 30 | 30 | 63 | 0.1 | 1.3 |
| 2 | NaBr | 30 | 17 | 59 | 0 | 1.5 |
| 3 | HBr | 20 | 36 | 55 | 0 | 0.2 |
| 4 | Br2 | 60 | 40 | 37 | 0 | 0.1 |
| 5 | LiBr . H2O | 45 | 38 | 64 | 0.2 | 2.6 |
| 6 | MgBr2 . 6H2O | 30 | 33 | 51 | 0.3 | 0.1 |
| 7 | AlBr3 . 6H2O | 45 | 29 | 41 | 0.2 | 0.1 |
| 8 | CoBr2 . 6H2O | 30 | 32 | 43 | 0.4 | 0.4 |
| 9 | n-C4H9Br | 120 | 17 | 32 | 0 | 0 |
| 10 | Bromobenzene | 120 | 5 | 25 | 0 | 0 |
| 11 | NH4Br | 30 | 32 | 58 | 0 | 1.1 |
| 12 | FeBr3 | 60 | 29 | 54 | 0 | 0.8 |
| 13 | CuBr2 | 45 | 16 | 61 | 0.1 | 0.5 |
| 14 | CH3COBr | 30 | 27 | 56 | 0 | 1.3 |

EXAMPLE 11

Using NaBr as bromine compound, the oxidation experiment was carried out in the same manner as described in Example 10 to investigate the influence of the reaction temperature and the conversion rate on the result of experiment. Table 11 shows the results obtained.

TABLE 11

| Exp. No. | Reaction Temperature (°C.) | Reaction time (min.) | Conversion rate (%) | Rate of selection (mol %) Aldehyde | Alcohol | Acetic ester |
|---|---|---|---|---|---|---|
| 1 | 30–34 | 120 | 19 | 76 | 0 | 5.7 |
| 2 | 30–32* | 60 | 17 | 78 | 0 | 1.0 |
| 3 | 42–45 | 60 | 22 | 68 | 0 | 1.0 |
| 4 | 60–62 | 90 | 69 | 53 | 0 | 1.5 |
| 5 | 85–87 | 30 | 37 | 61 | 0 | 2.0 |
| 6 | 102–104 | 20 | 44 | 57 | 1.0 | 5.0 |
| 7 | 110–115 (Referential Example) | 20 | 56 | 51 | 2.0 | 7.0 |
| 8 | 18–21 | 180 | 0 | — | — | — |

Remarks:
*0.03 molar proportion of acetaldehyde based on o-methoxytoluene was added.

EXAMPLE 12

Using acetic acid as solvent and both of cobalt acetate tetrahydrate and NaBr as catalyst, the oxidation experiment of o-methoxytoluene with oxygen was carried out under normal pressure in the same manner as described in Example 10 to investigate the amounts of acetic acid, Co and NaBr as well as the effect of adding acetaldehyde. The results obtained are shown in Table 12.

TABLE 12

| Exp. No. | Molar ratio to o-methoxytoluene | | | | | Reaction temperature (°C.) | Reaction time (min.) | Conversion rate (%) | Rate of selection (mol %) | | |
|---|---|---|---|---|---|---|---|---|---|---|---|
| | AcOH | Ac$_2$O | Co | NaBr | AcH | | | | Aldehyde | Alcohol | Acetic ester |
| 1 | 0 | 6 | 0.03 | 0.01 | 0.1*[1] | 70–74 | 150 | 21 | 31 | 1.0 | 17.0 |
| 2 | 0.5 | 0 | 0.03 | 0.01 | 0.2*[1] | 64–67 | 60 | 33 | 15 | 2.5 | 0 |
| 3 | 1.0 | 0 | 0.1*[2] | 0.01 | 0 | 85–87 | 30 | 39 | 41 | 0 | 0.7 |
| 4 | 2 | 0 | 0.05 | 0.01 | 0.03 | 76–84 | 60 | 53 | 53 | 8.0 | 0.8 |
| 5 | 3 | 0 | 0.1 | 0.01 | 0 | 108–112 | 360*[3] | 15 | 28 | 0 | 12.5 |
| 6 | 5*[4] | 0 | 0.1 | 0.1 | 0.1*[1] | 80–84 | 60 | 72 | 49 | 0 | 2.6 |
| 7 | 5 | 2 | 0.1 | 0.01 | 0.2 | 65–67 | 240*[3] | 17 | 41 | 4.0 | 21.0 |
| 8 | 8 | 2 | 0.1 | 0.08*[6] | 0 | 118–124 | 300*[3] | 19 | 40 | 0 | 39.0 |
| 9 | 8 | 0 | 0.2*[7] | 0.01 | 0.1*[1] | 97–102 | 360*[3] | 17 | 29 | 0 | 21 |
| 10 | 8*[8] | 0 | 0.1*[2] | 0.01 | 0 | 68–71 | 60 | 41 | 55 | 0 | 19.5*[9] |
| 11 | 8 | 0 | 0.01 | 0.01 | 0.03 | 60–62 | 270 | 10 | 29 | 3.0 | 0.7 |
| 12 | 8 | 2 | 0.01 | 0.001 | 0 | 60–67 | 300 | 12 | 7 | 0.5 | 4.5 |
| 13 | 8 | 2 | 0.1 | 0.01 | 0 | 60–62 | 60 | 35 | 63 | 0 | 24.0 |
| 14 | 10 | 0 | 0.2*[10] | 0.02 | 0 | 55–60 | 60 | 37 | 59 | 0 | 0.5 |
| 15 | 15 | 0 | 0.3*[11] | 0.0001 | 0.05*[12] | 50–53 | 110 | 11 | 32 | 0 | 2.5 |
| 16 | 15 | 0 | 0.3 | 0.03 | 0 | 57–60 | 60 | 61 | 51 | 0 | 0.5 |
| (Referential Examples) | | | | | | | | | | | |
| 17 | 8 | 0 | 0.1 | 0 | 0 | 60–62 | 300 | 7 | 0 | 0 | 0 |
| 18 | 8 | 0 | 0.01 | 0.001 | 0 | 60–64 | 120 | 0 | — | — | — |
| 19 | 0 | 0 | 0.05*[7] | 0.05 | 0.1 | 70–74 | 120 | 9 | 0.1 | 0 | 0 |

Remarks:
*[1] Paraldehyde was used in place of AcH.
*[2] Cobalt benzoate was used in place of cobalt acetate tetrahydride.
*[3] Air (flow rate: 300 ml/min) was used as oxidizing agent in place of oxygen.
*[4] n-Butyric acid was used in place of AcOH.
*[5] n-Butyrate
*[6] KBr was used in place of NaBr.
*[7] Cobalt (bivalent) acetylacetonate was used in place of cobalt acetate tetrahydrate.
*[8] Propionic acid was used in place of AcOH.
*[9] Propionate
*[10] Cobalt stearate was used in place of cobalt acetate tetrahydrate.
*[11] Cobalt nitrate hexahydrate was used in place of cobalt acetate tetrahydrate.
*[12] Methyl ethyl ketone was used in place of AcH.

EXAMPLE 13

Except that the starting material to be oxidized was p-methoxytoluene, the experiments were carried out in the same manner as described in Example 12 to obtain the results shown in Table 13. In these experiments, commercially available p-methoxytoluene was sufficiently purified in the same manner as described in Example 10 before use.

TABLE 13

| Exp. No. | Molar ratio to p-methoxytoluene | | | | Reaction temperature (°C.) | Reaction time (min.) | Conversion rate (%) | Rate of selection (mol %) | | |
|---|---|---|---|---|---|---|---|---|---|---|
| | AcOH | Co | NaBr | AcH | | | | Aldehyde | Alcohol | Acetic ester |
| 1 | 0.3 | 0.03 | 0.01 | 0.2*[1] | 62–66 | 45 | 24 | 18 | 12.0 | 1.3 |
| 2 | 1 | 0.05 | 0.01 | 0 | 72–74 | 30 | 36 | 25 | 13.0 | 1.3 |
| 3 | 2 | 0.001 | 0.01 | 0 | 72–80 | 300 | 14 | 17 | 2.5 | 2.8 |
| 4 | 2 | 0.05 | 0.01 | 0 | 60–64 | 40 | 34 | 47 | 17.0 | 2.5 |
| 5 | 2*[2] | 0.03 | 0.01 | 0.005*[3] | 80–84 | 45 | 49 | 41 | 12.0 | 0 |
| 6 | 5 | 0.05 | 0.005 | 0 | 70–72 | 20 | 11 | 60 | 20.0 | 0 |
| 7 | 5 | 0.05 | 0.005 | 0.03 | 70–71 | 70 | 57 | 50 | 10.0 | 5.0 |
| 8 | 5 | 0.05 | 0.005 | 0.03 | 38–42 | 500 | 56 | 60 | 0 | 1.0 |
| 9 | 5 | 0.05 | 0.005 | 0.03 | 28–30 | 240 | 13 | 71 | 0.1 | 0.5 |
| 10 | 5 | 0.05*[4] | 0.005 | 0.03 | 60–64 | 60 | 31 | 54 | 3.0 | 2.0 |
| 11 | 5 | 0.1 | 0.01 | 0 | 59–60 | 360*[5] | 18 | 60 | 17.0 | 0.1 |
| 12 | 10 | 0.01 | 0.005 | 0 | 70–75 | 300 | 10 | 43 | 0 | 8.0 |
| 13 | 10 | 0.05 | 0.5 | 0.03 | 50–55 | 240 | 44 | 57 | 0.1 | 3.4 |
| 14 | 10 | 0.1 | 0.01 | 0 | 98–104 | 45 | 54 | 48 | 2.0 | 11.0 |
| 15 | 10 | 0.1*[6] | 0.01 | 0 | 60–62 | 45 | 26 | 58 | 0.1 | 0 |
| 16 | 10 | 0.1 | 0.001 | 0.03 | 50–52 | 60 | 21 | 59 | 0.1 | 1.3 |
| 17 | 15 | 0.1 | 0.0001 | 0.005 | 60–64 | 60 | 29 | 55 | 0 | 2.0 |
| 18 | 4*[7] | 0.1 | 0.01 | 2.0*[1] | 65–72 | 120 | 31 | 17 | 0.5 | 0.3 |
| (Referential Examples) | | | | | | | | | | |
| 19 | 10*[7] | 0.1 | 0.01 | 0 | 60–64 | 240 | 17 | 0 | 0 | 0 |
| 20 | 10 | 0.001 | 0.0005 | 0 | 72–76 | 330 | 4 | 2 | 0 | 2.0 |

TABLE 13-continued

| Exp. No. | Molar ratio to p-methoxytoluene | | | | Reaction temperature (°C.) | Reaction time (min.) | Conversion rate (%) | Rate of selection (mol %) | | |
|---|---|---|---|---|---|---|---|---|---|---|
| | AcOH | Co | NaBr | AcH | | | | Aldehyde | Alcohol | Acetic ester |
| 21 | 15 | 0.3 | 0 | 0.03 | 42–44 | 120 | 0.9 | 6 | 0 | 0 |

Remarks:
*[1] Paraldehyde was used in place of AcH.
*[2] n-Butyric acid was used in place of AcOH.
*[3] Methyl ethyl ketone was used in place of AcH.
*[4] Cobalt naphthenate (10% by weight in cobalt content) was used in place of cobalt acetate tetrahydrate.
*[5] An air stream (flow rate: 300 ml/min.) was used as oxidizer in place of oxygen.
*[6] Cobalt nitrate hexahydrate was used in place of cobalt acetate tetrahydrate.
*[7] In these experiments, benzene was used as solvent in place of AcOH and cobalt (bivalent) acetylacetonate was used as catalyst in place of cobalt acetate tetrahydrate. In Examples of the present invention, the formation of aldehyde was recognized probably due to the reason that acetic acid was formed in situ from paraldehyde. In Referential Examples, the formation of aldehyde was not at all recognized probably due to the reason that lower fatty acids were not formed in situ.

EXAMPLE 14

Using acetic acid as solvent and cobalt acetate tetrahydrate as catalyst, the oxidation experiments of various compounds with oxygen was carried out under normal pressure to make comparison of the case wherein a bromine compound was present in or a bromine compound and a co-oxidizer were co-existent in the reaction system with the case wherein a bromine compound alone or together with a co-oxidizer was not present in the reaction system. The results obtained are shown in Table 14. The starting material was synthetized by reacting p-cresol with a bromohydrocarbon in the presence of a caustic alkali as condensing agent according to a usual method and sufficiently purified in the same manner as described in Example 10 before use. The reaction product was identified according to the GC-MS method.

TABLE 14

| Starting material | Molar ratio to starting material | | | | Reaction temperature (°C.) | Reaction time (min.) | Conversion rate (%) | Rate of selection (mol %) | | |
|---|---|---|---|---|---|---|---|---|---|---|
| | AcOH | Co | Bromine compound | Co-oxidizer | | | | Aldehyde | Alcohol | Acetic ester |
|  | 10 | 0.1 | 0 (Comp.Exp.) | 0 | 110–114 | 240 | 7 | 0 | 0 | 0 |
| | 10 | 0.1 | NaBr 0.03 | 0 | 60–63 | 90 | 49 | 65 | 0.5 | 0 |
| 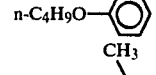 | 15 | 0.3 | 0 (Comp.Exp.) | 0 | 100–112 | 240 | 0 | — | — | — |
| | 15 | 0.3 | NaBr 0.03 | 0.03 paraldehyde | 70–74 | 60 | 40 | 61 | 0.5 | 0 |
| 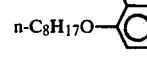 | 15 | 0.1 | 0 (Comp.Exp.) | 0 | 109–113 | 150 | 0 | — | — | — |
| | 15 | 0.1 | NaBr 0.01 | methyl ethyl ketone | 70–72 | 150 | 32 | 72 | 0.1 | 0 |
| | 15 | 0.1 | NaBr 0.05 | 0.03 ethyl ketone 0 | 100–105 | 150 | 12 | 56 | 0 | 3.0 |
|  | 15 | 0.3 | 0 (Comp.Exp.) | 0 | 109–111 | 150 | 0 | — | — | — |
| | 15 | 0.3 | NaBr 0.03 | methyl ethyl ketone 0.1 | 60–63 | 90 | 23 | 31 | 0 | 0.5 |
| 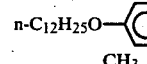 | 10 | 0.1 | 0 (Comp.Exp.) | 0 | 102–106 | 150 | 8 | 13 | 0 | 0 |
| | 10 | 0.1 | KBr 0.01 | 0.03 paraldehyde | 68–72 | 90 | 44 | 57 | 0.1 | 1.0 |
| 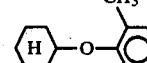 | 10 | 0.1 | 0 (Comp.Exp.) | 0 | 115–118 | 150 | 6 | 0 | 0 | 0 |
| | 10 | 0.1 | NaBr 0.01 | 0 | 58–60 | 150 | 15 | 12 | 3.0 | 0 |
| 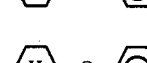 | 15 | 0.1 | 0 (Comp.Exp.) | 0 | 103–113 | 150 | 0 | — | — | — |
| | 15 | 0.1 | NaBr 0.01 | AcH 0.03 | 70–71 | 90 | 22 | 35 | 2.0 | 0 |
| 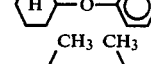 | 10 | 0.01 | (Comp.Exp.) NaBr 0.01 | 0 | 70–72 | 180 | 9 | 0 | 0 | 0 |
| | 8* | 0.01 | NaBr 0.01 | 0 | 70–72 | 180 | 11 | 16 | 0 | 2 |
| | 10 | 0.1 | 0 (Comp.Exp.) | 0 | 60–62 | 120 | 6 | 12 | 0 | 0 |
| | 10 | 0.1 | NaBr 0.01 | AcH 0.03 | 60–62 | 40 | 51 | 44 | 0.3 | 0.3 |
| | 10 | 0.1 | NaBr 0.01 | 0 | 60–62 | 50 | 33 | 45 | 1 | 0.5 |

Remarks:
*In this experiment, 2 molar proportion of acetic anhydride based on the starting material was used in addition to AcOH.

EXAMPLE 15

In a 300 ml SUS-316 stainless steel autoclave equipped with a stirrer, a thermometer and a gas inlet was placed 150 ml of the liquid starting material mixture having a given composition. The mixture was heated up to a given temperature while vigorously stirring the mixture at a rotation speed of 1600 rpm. From a pressure tank, oxygen was then introduced through a pressure regulator into the mixture to keep the oxygen pressure to 1.5 kg/cm² (absolute pressure). The amount of oxygen consumed was roughly calculated from the decrease in the oxygen pressure in the pressure tank and the reaction was interrupted by rapidly cooling the reactor at the stage where a given amount of oxygen was absorbed in the starting material. The reaction product was analyzed in the same manner as described in Example 1. The results of the experiments are shown in Table 15.

cobalt acetate tetrahydrate and various bromine compounds in an amount of 3 mol% to the m-phenoxytoluene. The liquid mixture was heated up to a given temperature and an oxygen stream was then introduced from a pressure tank through a pressure regulator into the mixture while stirring it vigorously at a rotation speed of 1600 rpm. The inner pressure of oxygen was kept at 20 kg/cm². As soon as the gaseous oxygen was introduced or after the lapse of a short intuction period,

TABLE 15

| Exp. No. | Starting compound | Molar ratio to starting material | | | | Reaction temperature (°C.) | Reaction time (min.) | Reaction rate (%) | Rate of selection | | |
|---|---|---|---|---|---|---|---|---|---|---|---|
| | | AcOH | Co*¹ | Br*² | Co-oxidizer | | | | aldehyde | Alcohol | Acetic ester |
| 1 | MeO—◯—Me | 5 | 0.05 | 0.005 | 0 | 70–76 | 15 | 53 | 62 | 1.2 | 0 |
| 2 | CH₃ / MeO—◯ | 8 | 0.1 | 0.01 | AcH 0.2 | 60–61 | 40 | 33 | 52 | 0 | 0 |
| 3 | n-C₈H₁₇O—◯—CH₃ | 10 | 0.1 | 0.01 | PA*³ 0.03 | 80–82 | 20 | 38 | 59 | 1.5 | 0 |
| 4 | n-C₈H₁₇O—◯—CH₃ | 10*⁴ | 0.05 | 0.001 | 0 | 150–158 | 6 | 51 | 43 | 1.8 | 0.04*⁵ |

Remarks:
*¹Cobalt acetate tetrahydrate was used.
*²NaBr was used.
*³Paraldehyde
*⁴n-Butyric acid was used in place of AcOH.
*⁵n-Butyrate

EXAMPLE 16

Using p-n-octyloxytoluene as starting material, AcOH as solvent, NaBr as bromine compound and cobalt acetate tetrahydrate as cobalt salt, the experiments were carried out in the same manner as described in Example 10. The results of experiments obtained are shown in Table 16.

a violent oxidation reaction place so that it was difficult to maintain the reaction temperature at a definite temperature range. However, careful attention was paid to maintain the reaction temperature as definite as possible by warming or cooling and the quantity of oxygen consumed was roughly calculated from decrease in the pressure of oxygen in the oxygen pressure tank. At the time an almost required quantity of oxygen was ab-

TABLE 16

| Exp. No. | Molar ratio to starting material | | | | | Reaction temperature (°C.) | Reaction time (min.) | Conversion rate (%) | Rate of selection (mol %) | | |
|---|---|---|---|---|---|---|---|---|---|---|---|
| | AcOH | Co | Br | Co-oxidizer | | | | | Aldehyde | Alcohol | Acetic ester |
| 1 | 10 | 0.01 | 0.01 | | 0 | 100–105 | 60 | 64 | 52 | 3.0 | 0.1 |
| 2 | 10 | 0.1 | 0.01 | MEK*¹ | 0.03 | 80–83 | 240 | 17 | 62 | 2.0 | 0 |
| 3 | 10 | 0.01 | 0.01 | | 0 | 100–102 | 120 | 11 | 18 | 0 | 0 |
| 4 | 0.5 | 0.03 | 0.01 | PA*² | 0.1 | 110–116 | 120 | 14 | 37 | 11 | 1.5 |
| | (Referential Example) | | | | | | | | | | |
| 5 | 10 | 0.1 | 0 | | 0 | 110–115 | 400 | 0 | — | — | — |
| | (Comparative Example) | | | | | | | | | | |
| 6 | 10 | 0.1 | 0.01 | | 0 | 80–82 | 240 | 3 | 0 | 0 | 0 |

Remarks:
*¹Methyl ethyl ketone
*²Paraldehyde

EXAMPLE 17

In a 300 ml SUS-316 stainless autoclave equipped with a stirrer, a thermometer and a gas inlet were placed 30 g of m-phenoxytoluene, 120 g of acetic acid, 12 g of sorbed, the reactor was quickly cooled to stop the reaction. The reaction product was analyzed in a similar manner to that described in Example 1. The results obtained are shown in Table 17.

TABLE 17

| Exp. No. | Bromine compound | Reaction*¹ temperature (°C.) | Reaction time | Conversion rate (%) | Rate of selection (mol %) | | |
|---|---|---|---|---|---|---|---|
| | | | | | Aldehyde | Alcohol | Acetic ester |
| 1 | HBr (aqueous*² solution) | 100–136 | 55 sec. | 61 | 24 | 17 | 1 |
| 2 | KBr | 103–137 | 50 sec. | 59 | 37 | 13 | 2 |
| 3 | NaBr | 100–131 | 45 sec. | 64 | 23 | 29 | 3 |
| 4 | MgBr₂ . 6H₂O | 118–142 | 1 min. 20 sec. | 46 | 26 | 11 | 1 |

TABLE 17-continued

| Exp. No. | Bromine compound | Reaction*[1] temperature (°C.) | Reaction time | Conversion rate (%) | Rate of selection (mol %) | | |
|---|---|---|---|---|---|---|---|
| | | | | | Aldehyde | Alcohol | Acetic ester |
| 5 | LiBr . H$_2$O | 105–129 | 1 min. 5 sec. | 61 | 24 | 20 | 2 |
| 6 | CoBr$_2$ . 6H$_2$O | 123*[3]–155 | 2 min. | 74 | 19 | 7 | 0.2 |
| 7 | Bromobenzene | 152*[3]–160 | 17 min. | 39 | 28 | 13 | 0.1 |
| 8 | n-Butyl bromide | 169*[3]–190 | 40 sec. | 47 | 29 | 4 | 0.1 |
| 9 | Br$^2$ | 100–131 | 50 sec. | 61 | 23 | 16 | 1 |
| 10 | AlBr$_3$ . 6H$_2$O | 120–148 | 1 min. 10 sec. | 52 | 21 | 11 | 3 |
| 11 | NH$_4$Br | 102–134 | 55 sec. | 57 | 32 | 17 | 2 |
| 12 | FeBr$_3$ | 122–151 | 1 min. 35 sec. | 64 | 19 | 9 | 0.5 |
| 13 | CuBr$_2$ | 125–156 | 1 min. 50 sec. | 62 | 23 | 8 | 0.2 |
| 14 | CH$_3$COBr (Comparative Example) | 100–133 | 45 sec. | 59 | 27 | 14 | 2 |
| 15 | None | 183–232*[4] | 1 min. 10 sec. | 45 | 6 | 0 | 0 |

Remarks:
*[1]The maximum and minimum temperatures during the reaction are shown.
*[2]A commercially available reagent of special grade (47–48% in purity as aqueous solution) was used as such.
*[3]The reaction did not take place unless the temperature was elevated up to this temperature.
*[4]The reaction did not start below this temperature. This experiment was carried out at an oxygen pressure of 45 kg/cm$^2$.

EXAMPLE 18

Using NaBr as bromine compound, the experiments were carried out to investigate the influence of the quantity of NaBr added on the results. Table 18 shows the results obtained. Except for the quantity of NaBr added, the reaction conditions adopted in this example were quite identical with those adopted in Example 17.

TABLE 18

| Exp. No. | NaBr m-phenoxytoluene (molar ratio) | Reaction temperature (°C.) | Reaction time | Conversion rate (%) | Rate of selection (mol %) | | |
|---|---|---|---|---|---|---|---|
| | | | | | Aldehyde | Alcohol | Acetic ester |
| 1 | 0.0001*[1] | 150–180*[3] | 124 min. | 7 | 0.1 | 30 | 0 |
| 2 | 0.003 | 129–138 | 1 min. | 31 | 40 | 5 | 0.1 |
| 3 | 0.01 | 124–148 | 50 sec. | 55 | 28 | 15 | 0 |
| 4 | 0.03 | 100–131 | 45 sec. | 64 | 23 | 29 | 3 |
| 5 | 0.3 | 100–130 | 1 min. 10 sec. | 63 | 25 | 17 | 3 |
| 6 | 0.5*[2] | 144–156*[3] | 25 min. | 19 | 10 | 0.1 | 0 |

Remarks:
*[1]The reaction liquid was composed of 60 g of m-phenoxytoluene, 80 g of acetic acid and 0.08 g of cobalt acetate tetrahydrate.
*[2]The amount of cobalt acetate tetrahydrate added was 1.2 g.
*[3]As the reaction velocity was slow, the mixture was gradually heated to this temperature.

EXAMPLE 19

Except that the ratio of Co to NaBr was varied, the experiments were carried out in the same manner as described in Example 18. The results obtained are shown in Table 19. The majority of the data in this table corresponds to the data in Table 6 shown in terms of the ratio of Co to NaBr added.

TABLE 19

| Exp. No. | NaBr Co(OAC)$_2$ . 4H$_2$O (molar ratio) | Reaction temperature (°C.) | Reaction time | Conversion rate (%) | Rate of selection (mol %) | | |
|---|---|---|---|---|---|---|---|
| | | | | | Aldehyde | Alcohol | Acetic ester |
| 1 | 0.001 | 160*[1]–170 | 2 min. 5 sec. | 51 | 17 | 0.1 | 0 |
| 2 | 0.01 | 129–138 | 1 min. | 31 | 40 | 5 | 0.1 |
| 3 | 0.1 | 100–131 | 45 sec. | 64 | 23 | 29 | 3 |
| 4 | 1 | 100–130 | 1 min. 10 sec. | 63 | 25 | 17 | 3 |
| 5 | 8 | 130–141 | 4 min. 35 sec. | 49 | 25 | 10 | 1 |
| 6 | 17*[2] | 144–156*[3] | 25 min. | 19 | 10 | 0.1 | 0 |

Remarks:
*[1]The reaction did not take place below this reaction temperature.
*[2]The amount of cobalt acetate tetrahydrate was 1.2 g.
*[3]As the reaction velocity was slow, the mixture was gradually heated to this temperature.

EXAMPLE 20

Except that the bromine compound was NaBr and the amount of Co salt was varied, the experiments were carried out in the same manner as described in Example 17 to investigate the influence of the amount of Co salt. The results obtained are shown in Table 20.

TABLE 20

| Exp. No. | Co(OAc)$_2$·4H$_2$O m-phenoxytoluene (molar ratio) | Reaction temperature (°C.) | Reaction time | | Conversion rate (%) | Rate of selection (mol %) | | |
|---|---|---|---|---|---|---|---|---|
| | | | | | | Aldehyde | Alcohol | Acetic ester |
| 1 | 0.01 | 100–121* | 45 min. | | 21 | 30 | 4 | 0 |
| 2 | 0.03 | 100–137* | 30 min. | | 35 | 39 | 8 | 0.1 |
| 3 | 0.1 | 100–128 | 1 min. | 25 sec. | 47 | 30 | 12 | 2 |
| 4 | 0.3 | 100–131 | | 45 sec. | 64 | 23 | 29 | 3 |
| 5 | 0.5 | 100–137 | | 55 sec. | 67 | 20 | 14 | 2 |

Remarks:
*The reaction temperature was slowly elevated.

EXAMPLE 21

Experiments were carried out under such condition that the mixing ratio of m-phenoxytoluene to acetic acid was varied. Using as catalysts 3 mol% of cobalt acetate tetrahydrate and 3 mol% of sodium bromide to m-phenoxytoluene and limiting the total volume of the reaction liquid to 150 ml, the experiments were carried out in the same manner as described in Example 17. The results obtained are shown in Table 21. No substantial intermediate oxidation product was obtained when the amount of acetic acid was zero. When the amount of acetic acid was 0.5 mol per mol of m-phenoxytoluene, m-phenoxybenzaldehyde was obtained at a rate of selection of 20 mol% at a conversion rate of 30%. However, this experiment showed bad reproducibility.

TABLE 21

| Exp. No. | AcOH m-phenoxytoluene (molar ratio) | Reaction temperature (°C.) | Reaction time | | Conversion rate (%) | Rate of selection (mol %) | | |
|---|---|---|---|---|---|---|---|---|
| | | | | | | Aldehyde | Alcohol | Acetic ester |
| 1 | 1 | 138–174 | 1 min. | 10 sec. | 34 | 35 | 5 | 0.1 |
| 2 | 5 | 135–166 | 2 min. | 15 sec. | 43 | 31 | 6 | 0.1 |
| 3 | 5*[1] | 140–163 | 1 min. | 10 sec. | 22 | 24 | 2 | 7.5 |
| 4 | 5*[2] | 133–160 | 1 min. | 07 sec. | 49 | 35 | 3 | 0.5 |
| 5 | 8*[3] | 135–157 | 1 min. | 30 sec. | 44 | 32 | 7 | 2.5 |
| 6 | 10*[4] | 140–168 | 1 min. | 05 sec. | 31 | 34 | 9 | 0.5*[5] |
| 7 | 12.5 | 100–137*[6] | 30 min | | 34 | 39 | 8 | 0.1 |
| 8 | 15*[7] | 145–164 | 0 min. | 55 sec. | 36 | 27 | 6 | 0.1*[8] |

Remarks:
*[1]Acetic anhydride was used in place of acetic acid and cobalt (bivalent) acetylacetonate was used in place of cobalt acetate tetrahydrate.
*[2]Cobalt nitrate hexahydrate in an amount of 10 mol % based on m-phenoxytoluene was used in place of cobalt acetate tetrahydrate and aluminum bromide hexahydrate was used in place of sodium bromide.
*[3]Aluminum bromide was used as bromine compound and acetic anhydride in an amount of 2 mols per mol of m-phenoxytoluene was added to the liquid of a standard composition in which the amount of acetic acid is 8 mols per mol of m-phenoxytoluene used.
*[4]Propionic acid was used in place of acetic acid and cobalt benzoate was used in place of cobalt acetate tetrahydrate.
*[5]Propionate
*[6]The reaction mixture was gradually heated to this temperature to increase the reaction velocity.
*[7]n-Butyric acid was used in place of acetic acid and cobalt stearate was used in place of cobalt acetate tetrahydrate.
*[8]n-Butyrate

EXAMPLE 22

Except that the pressure of oxygen was varied and the bromine compound was all NaBr, the experiments were carried out under the same conditions as described in Example 17. The results obtained are shown in Table 22.

TABLE 22

| Exp. No. | Oxygen pressure (kg/cm$^2$) | Reaction temperature (°C.) | Reaction time | | Conversion rate (%) | Rate of selection (mol %) | | |
|---|---|---|---|---|---|---|---|---|
| | | | | | | Aldehyde | Alcohol | Acetic ester |
| 1 | 3 | 120–123 | 60 min. | | 46 | 20 | 32 | 0.1 |
| 2 | 5 | 116–122 | 3 min. | 30 sec. | 60 | 36 | 13 | 0.1 |
| 3 | 20 | 100–131 | | 45 sec. | 64 | 23 | 29 | 3 |
| 4 | 45 | 100–135 | | 25 sec. | 60 | 32 | 11 | 2 |

EXAMPLE 23

In Example 17 using NaBr as bromine compound, various co-oxidizers were added to the liquid starting material mixture and the experiments were carried out at 50° C. The results obtained are shown in Table 23.

TABLE 23

| Exp. No. | Co-oxidizer | Amount*[1] | Reaction temperature (°C.) | Reaction time (min.) | Conversion rate (%) | Rate of selection (mol %) | | |
|---|---|---|---|---|---|---|---|---|
| | | | | | | Aldehyde | Alcohol | Acetic ester |
| 1 | none | | 50–55 | 120 | 20 | 58 | 16 | 0.1 |
| 2 | Paraldehyde | 0.02 | 52–52.3 | 65 | 21 | 59 | 31 | 0.1 |
| 3 | " | 0.005 | 51–52 | 85 | 21 | 59 | 24 | 0.1 |
| 4 | " | 0.0001 | 50–53 | 100 | 23 | 58 | 27 | 0.1 |
| 5 | Methyl ethyl ketone | 0.06 | 54–59 | 50 | 22 | 58 | 23 | 0 |

TABLE 23-continued

| Exp. No. | Co-oxidizer | Amount*[1] | Reaction temperature (°C.) | Reaction time (min.) | Conversion rate (%) | Rate of selection (mol %) | | |
|---|---|---|---|---|---|---|---|---|
| | | | | | | Aldehyde | Alcohol | Acetic ester |
| 6 | Acetaldehyde*[2] | 0.08 | 50-56 | 55 | 17 | 51 | 29 | 0.1 |
| 7 | " | " | 51-54 | 120 | 19 | 36 | 28 | 0.5 |

Remarks:
*[1]The amount of co-oxidizer added was shown in terms of molar proportion to m-phenoxytoluene.
*[2]The liquid starting material mixture had the following composition: m-phenoxytoluene : acetic acid : cobalt acetate tetrahydrate : NaBr : acetaldehyde = 120 : 20 : 4 : 0.3 : 2.5 (g)

EXAMPLE 24

In Example 23 using paraldehyde as co-oxidizer, the experiments were carried out to investigate the influence of reaction temperature. The results obtained are shown in Table 24.

TABLE 24

| Exp. No. | Reaction temperature (°C.) | Reaction time | Conversion rate (%) | Rate of selection (mol %) | | |
|---|---|---|---|---|---|---|
| | | | | Aldehyde | Alcohol | Acetic ester |
| 1 | 52-52.3 | 65 min. | 21 | 59 | 31 | 0.1 |
| 2 | 72-89 | 7 min. | 50 | 36 | 13 | 0.1 |
| 3 | 99-108 | 42 sec. | 63 | 28 | 12 | 0.1 |
| 4 | 121-147 | 25 sec. | 54 | 31 | 7 | 0.1 |

EXAMPLE 25

In the same manner as described in Example 17 o-phenoxytoluene was synthetized from o-cresol. In addition, m-methoxytoluene and p-methoxytoluene were prepared according to a usual method by methylating m-cresol and p-cresol, respectively, with dimethyl sulfate. These products were completely purified by washing with a diluted aqueous solution of alkali and distillation under reduced pressure to prepare the starting materials in this example. To compare the case where sodium bromide was present in the reaction system with the case wherein sodium bromide was absent in the reaction system, the experiments were carried out in the presence or absence of sodium bromide by using the following alternative two compositions:

starting material:acetic acid:cobalt acetate tetrahydrate = 1:12.5:0.3 (molar proportion) for m-methoxytoluene or 1:10:0.1 (molar proportion) for p-methoxytoluene.

The results obtained are shown in Table 25. The oxidation of p-methoxytoluene was carried out under an oxygen pressure of 45 kg/cm$^2$ while the other case under 20 kg/cm$^2$. The amount of sodium bromide added was 0.01 mol (in the case of oxidizing p-methoxytoluene) or 0.03 mol (in the case of oxidizing the m-isomer) per mol of the starting material. The other reaction conditions were quite identical with those described in Example 21.

TABLE 25

| Exp. No. | Amount of NaBr added | Reaction temperature (°C.) | Reaction time | Conversion rate (%) | Rate of selection (mol %) | | |
|---|---|---|---|---|---|---|---|
| | | | | | Aldehyde | Alcohol | Acetic ester |
| 1 | (Oxidation of m-methoxytoluene) | | | | | | |
| 2 | 0* | 120-126 | 40 min. | 23 | 17 | 0 | 0 |
| 3 | 0.03** | 101-120 | 45 sec. | 52 | 44 | 6 | 0.1 |
| | (Oxidation of p-methoxytoluene) | | | | | | |
| 4 | 0* | 65-70 | 360 min. | 21 | 37 | 0.3 | 1.2 |
| 5 | 0.01** | 62-63 | 120 min. | 67 | 78 | 1 | 0 |
| | (Oxidation of o-phenoxytoluene) | | | | | | |
| 6 | 0* | 150-181*** | 60 min. | 6 | 4 | 0 | 0 |
| 7 | 0.03** | 148-174 | 42 sec. | 56 | 35 | 2 | 3 |

Remarks:
*Comparative example
**Example
***The reaction temperature was elevated to 131° C. since the reaction did not take place at 150° C.

EXAMPLE 26

To compare the case wherein sodium bromide was present in the reaction system with the case wherein sodium bromide was absent in the reaction system, the oxidation reaction of a starting compound was carried out in the same reactor as used in Example 17 by using 25 g of the starting compound, acetic acid in an amount of 12.5 mols per mol of the starting compound and cobalt acetate tetrahydrate in an amount of 0.3 mol per mol of the starting compound in the presence or absence of sodium bromide under an oxygen pressure of 20 kg/cm$^2$. The results obtained are shown in Table 26.

The starting compound used was synthetized in the same manner as described in Example 17 from o-, m- or p-cresol and a bromohydrocarbon. The identification of the reaction product was performed according to the GC-MS method.

TABLE 26

| Exp. No. | Starting material | Amount of NaBr added[*1] | | Reaction temperature (°C.) set value | Reaction temperature (°C.) max. value | Reaction time | Conversion rate (%) | Rate of selection[*2] (mol %) Aldehyde | Rate of selection[*2] (mol %) Alcohol | Rate of selection[*2] (mol %) Acetic ester |
|---|---|---|---|---|---|---|---|---|---|---|
| 1 | n-C₃H₇O–C₆H₄–CH₃ | 0 | (Comparative Example) | 171[*3]–182 | | 40 sec. | 38 | 2 | 0.5 | 0.1 |
| | | 0.03 | (Example) | 100–110 | | 43 sec. | 57 | 26 | 1 | 2 |
| 2 | n-C₄H₉O–C₆H₄–CH₃ | 0 | (Comparative Example) | 177[*3]–187 | | 30 sec. | 11 | 4 | 2 | 0 |
| | | 0.03 | (Example) | 120–134 | | 45 sec. | 54 | 44 | 2 | 2 |
| 3 | iso-C₄H₉O–C₆H₄–CH₃ | 0 | (Comparative Example) | 160–180[*4] | | 40 min. | 0 | — | — | — |
| | | 0.03 | (Example) | 101–125 | | 1 min. | 44 | 41 | 0 | 2 |
| 4 | n-C₄H₉O–C₆H₄–CH₃ | 0 | (Comparative Example) | 170[*3]–179 | | 55 sec. | 15 | 40 | 0.3 | 5 |
| | | 0.03 | (Example) | 141–162 | | 1 min. | 59 | 54 | 1 | 4 |
| 5 | n-C₄H₉O–C₆H₄–CH₃ | 0 | (Comparative Example) | 132[*3]–152 | | 50 sec. | 66 | 68 | 2 | 9 |
| | | 0.03 | (Example) | 94–106 | | 1 min. 40 sec. | 80 | 73 | 0 | 3.5 |
| 6 | n-C₈H₁₇O–C₆H₄–CH₃ | 0 | (Comparative Example) | 177[*3]–188 | | 15 sec. | 10 | 14 | 14 | 1 |
| | | 0.03[*5] | (Example) | 124–153 | | 40 sec. | 59 | 38 | 5 | 0.1 |
| 7 | n-C₈H₁₇O–C₆H₄–CH₃ | 0 | (Comparative Example) | 175[*3]–184 | | 40 sec. | 8 | 50 | 0 | 6 |
| | | 0.03 | (Example) | 102–119 | | 1 min. 10 sec. | 59 | 68 | 0.1 | 1 |
| 8 | n-C₁₂H₂₅O–C₆H₄–CH₃ | 0 | (Comparative Example) | 160[*3]–186 | | 25 sec. | 72 | 54 | 0.1 | 3 |
| | | 0.03 | (Example) | 117–136 | | 1 min. 45 sec. | 55 | 62 | 0.5 | 0.1 |
| | | 0.01 | (Example) | 130–159 | | 50 sec. | 79 | 60 | 1 | 0.5 |
| 9 | C₆H₁₁O–C₆H₄–CH₃ | 0 | (Comparative Example) | 172[*3]–189 | | 30 sec. | 17 | 23 | 0.1 | 4 |
| | | 0.03 | (Example) | 107–129 | | 50 sec. | 67 | 28 | 0.2 | 15 |
| 10 | H₃C–C₆H₄–O–C₆H₄–CH₃ | 0 | (Comparative Example) | 168[*3]–179 | | 43 sec. | 15 | 26 | 10 | 3 |
| | | 0.03 | (Example) | 101–132 | | 35 sec. | 75 | 29 | 2 | 0.4 |
| 11 | (CH₃)C₆H₄–O–C₆H₄(CH₃) | 0 | (Comparative Example) | 170[*3]–177 | | 40 sec. | 17 | 10 | 0.1 | 0 |

TABLE 26-continued

| Exp. No. | Starting material | Amount of NaBr added*1 | Reaction temperature (°C.) set value | Reaction temperature (°C.) max. value | Re-action time | Con-version rate (%) | Rate of selection*2 (mol %) Al-dehyde | Rate of selection*2 (mol %) Al-cohol | Rate of selection*2 (mol %) Acetic ester |
|---|---|---|---|---|---|---|---|---|---|
|  |  | 0.03 (Example) | 139–156 |  | 35 sec. | 49 | 44 | 8 | 4 |

Remarks:
*1Shown in terms of molar ratio to the starting compound
*2The rate of selection to aldehyde, alcohol or acetic ester which was formed by oxidation of only one methyl group or one of the methyl groups bound directly to the benzene ring is shown.
*3The reaction did not take place below this reaction temperature.
*4Although the reaction temperature was slowly elevated up to 180° C., the reaction did not take place.
*5Paraldehyde in an amount of 2 mol % based on the starting compound was added as co-oxidizer.

EXAMPLE 27

Except that sodium bromide was used as bromine compound, that various cobalt salts were added in an amount of 0.1 mol per mol of the starting compound and that the oxygen pressure was 7 kg/cm$^2$, the oxidation reactions of o- and p-phenoxytoluenes were carried out in the same manner as described in Example 17. The results obtained are shown in Tables 27(a) and 27(b).

70°–80° C. and a stream of oxygen was introduced at a flow rate of 3.6 liters/hr into the mixture while stirring it vigorously at a rotation speed of 1000–1200 rpm. The reaction was carried out for a given period of time. The reaction liquid was analyzed according to gas chromatography at elevated temperatures using as a filler silane-treated Chromosolve on which 7% by weight of Silicone oil OV-17 had been carried. The results of experiments are shown in Table 28. 3,4-Dimethoxytol- TABLE 27(a)

| | Oxidation of o-phenoxytoluene | | | | | |
|---|---|---|---|---|---|---|
| Cobalt salt | Reaction temperature (°C.) | Reaction time | Conversion rate (%) | Rate of selection (mole %) Aldehyde | Alcohol | Acetic ester |
| Acetylacetonate (bivalent) | 130–136 | 2 min. 25 sec. | 28 | 57 | 1 | 3 |
| Naphthenate* | 152–172 | 2 min. 30 sec. | 37 | 39 | 2 | 5 |
| Benzoate | 146–151 | 3 min. 05 sec. | 46 | 43 | 1 | 4 |
| Nitrate (hexahydrate) | 135–142 | 5 min. 10 sec. | 49 | 33 | 1 | 1 |

Remarks:
*10% by weight in cobalt content

TABLe 27(b)

| | Oxidation of p-phenoxytoluene | | | | | |
|---|---|---|---|---|---|---|
| Cobalt salt | Reaction temperature (°C.) | Reaction time | Conversion rate (%) | Rate of selection (mol %) Aldehyde | Alcohol | Acetic ester |
| Acetylacetonate | 80–87 | 1 min. 50 sec. | 32 | 68 | 3 | 3 |
| Naphthenate*1 | 75–83 | 2 min. 10 sec. | 43 | 56 | 1 | 0.5 |
| Benzoate | 78–84 | 1 min. 45 sec. | 37 | 64 | 0.5 | 2 |
| Stearate | 82–90 | 2 min. 55 sec. | 46 | 59 | 0.5 | 2 |
| Nitrate (hexahydrate) | 85–93 | 2 min. 05 sec. | 51 | 52 | 1 | 1 |
| Hydroxide*2 | 76–85 | 2 min. 00 sec. | 42 | 58 | 1 | 1 |
| Bromide (hexahydrate)*3 | 78–86 | 1 min. 55 sec. | 35 | 62 | 1 | 2 |

Remarks:
*110% by weight in cobalt content
*260% by weight in cobalt content
*3In addition to cobalt bromide hexahydrate, sodium acetate was added in an amount of 0.2 mol per mol of p-phenoxytoluene.

EXAMPLE 28

In a 500 ml Pyrex glass 4-necked flask equipped with a stirrer, a thermometer, a gas inlet, a reflux condenser and a gas outlet was placed 150 ml of a liquid starting material mixture composed of 3,4-dimethoxytoluene, acetic acid, cobalt acetate tetrahydrate, a bromine compound and paraldehyde in a proportion of 1:12.5:0.3:0.03:0.05 (molar ratio). The mixture was maintained in a hot water bath at a temperature of uene used as starting material was synthetized according to a usual method by methylating homocatechol with dimethyl sulfate and purified before use by boiling the crude product with a 30% aqueous solution of caustic soda for about 3 hours, washing the product with water, distilling the product under reduced pressure, washing the distillate first with a 20% aqueous solution of caustic soda then thoroughly with water, distilling the product under reduced pressure and drying the distillate with calcium chloride.

TABLE 28

| Exp. No. | Bromine compound | Reaction temperature (°C.) | Reaction time (min) | Conversion rate (%) | Rate of selection (mol %) Aldehyde | Alcohol | Acetic ester |
|---|---|---|---|---|---|---|---|
| 1 | HBr*1 | 80–82 | 45 | 44.3 | 40.7 | 3.2 | 6.6 |
| 2 | KBr | 70–73 | 60 | 40.2 | 47.3 | 1.0 | 4.7 |

TABLE 28-continued

| Exp. No. | Bromine compound | Reaction temperature (°C.) | Reaction time (min) | Conversion rate (%) | Rate of selection (mol %) | | |
|---|---|---|---|---|---|---|---|
| | | | | | Aldehyde | Alcohol | Acetic ester |
| 3 | NaBr*² | 70–74 | 90 | 49.8 | 39.2 | 0.1 | 1.5 |
| 4 | NaBr*³ | 70–75 | 60 | 40.1 | 48.4 | 0.5 | 6.3 |
| 5 | NaBr*⁴ | 80–84 | 45 | 46.3 | 41.2 | 2.3 | 9.6 |
| 6 | NaBr*⁵ | 70–73 | 60 | 47.2 | 46.7 | 1.0 | 4.3 |
| 7 | AlBr₃ . 6H₂O | 71–74 | 60 | 42.2 | 45.8 | 1.0 | 7.1 |
| 8 | Br₂ | 70–73 | 60 | 28.3 | 37.2 | 0.5 | 1.2 |
| 9 | CoBr₂ . 6H₂O | 70–74 | 60 | 46.1 | 48.4 | 0.5 | 4.9 |
| 10 | FeBr₃ | 70–74 | 60 | 46.2 | 44.3 | 1.2 | 2.4 |
| 11 | CuBr₂ | 70–73 | 60 | 40.3 | 43.2 | 1.1 | 3.8 |
| 12 | CH₃COBr | 70–73 | 60 | 39.7 | 40.1 | 1.5 | 2.3 |
| 13 | Bromobenzene | 80–83 | 60 | 19.7 | 23.1 | 0 | 0 |
| 14 | n-C₄H₉Br | 80–83 | 60 | 20.4 | 26.8 | 0.1 | 0.1 |
| 15 | LiBr . H₂O | 70–73 | 60 | 47.2 | 46.6 | 1.5 | 3.2 |
| 16 | MgBr₂ . 6H₂O | 70–74 | 60 | 41.8 | 45.1 | 1.0 | 4.3 |
| 17 | NH₄Br | 70–72 | 60 | 38.4 | 33.5 | 0.5 | 5.2 |
| (Comparative Example) | | | | | | | |
| 18 | None*⁶ | 70–72 | 300 | 46.3 | 12.7 | 0.3 | 1.8 |

Remarks:
*¹A commercially available reagent of special grade (purity: 47–48% as an aqueous solution) was used as such.
*²Paraldehyde was not added.
*³The amount of paraldehyde added was 0.1 mol per mol of the starting compound.
*⁴Methyl ethyl ketone was added in place of paraldehyde.
*⁵Acetaldehyde was added in place of paraldehyde.
*⁶Paraldehyde was also not added.

EXAMPLE 29

Except that sodium bromide was used as bromine compound and the reaction conditions concerning the amount of paraldehyde and the reaction temperature were varied, the oxidation reaction of 3,4-diethoxytoluene with oxygen under normal pressure was carried out in the same manner as described in Example 28. The results obtained are shown in Table 29. 3,4-Diethoxytoluene used as starting material was synthetized according to a usual method by O-ethylating homocatechol with diethyl sulfate and fully purified before use in the same manner as described in Example 28.

TABLE 29

| Exp. No. | PA*¹ molar ratio | Reaction temperature (°C.) | Reaction time (min.) | Conversion rate (%) | Rate of selection (mol %) | | |
|---|---|---|---|---|---|---|---|
| | | | | | Aldehyde | Alcohol | Acetic ester |
| 1 | 0 | 70–71 | 90 | 54.2 | 38.4 | 0.1 | 1.0 |
| 2 | 0.1** | 80–82 | 150 | 53.7 | 38.4 | 1.0 | 7.0 |
| 3 | 0.1 | 70–74 | 60 | 38.8 | 46.6 | 1.0 | 5.2 |
| 4 | 0.1*² | 72–74 | 60 | 41.3 | 46.3 | 0.9 | 15.9 |
| 5 | 0.1 | 45–47 | 270 | 21.6 | 19.8 | 0 | 2.3 |
| 6 | 0.005 | 70–76 | 60 | 41.4 | 36.2 | 0.7 | 5.8 |
| 7 | 0.01** | 70–84 | 120 | 50.2 | 31.2 | 1.0 | 10.3 |
| 8 | 0.05 | 80–82 | 300*³ | 36.6 | 31.4 | 1.8 | 17.2 |
| 9 | 0*⁴ | 72–76 | 80 | 48.7 | 39.1 | 0 | 4.0 |
| 10 | 0*⁵ | 70–74 | 80 | 50.6 | 33.2 | 0.1 | 1.8 |
| 11 | 0*⁶ | 72–75 | 80 | 52.1 | 36.2 | 0.4 | 1.1 |
| 12 | 0*⁷ | 73–77 | 90 | 46.3 | 34.2 | 0.1 | 0.6 |
| 13 | 0*⁸ | 70–74 | 90 | 52.9 | 37.2 | 0 | 1.2 |
| 14 | 0.05*⁹ | 70–74 | 60 | 50.6 | 49.3 | 1.5 | 9.6 |
| 15 | 0*¹⁰ | 90–92 | 45 | 44.7 | 38.2 | 0.3 | 6.1 |
| (Referential Example) | | | | | | | |
| 16 | 0** | 100–108 | 200 | 32.0 | 14.5 | 0 | 6.8 |
| 17 | 0.1 | 35–37 | 400 | 12.1 | 1.5 | 0 | 0 |
| 18 | 3.0*¹¹ | 70–74 | 120 | 23.2 | 10.8 | 0.5 | 1.2 |
| 19 | 0*¹¹ | 75–77 | 300 | 0 | — | — | — |

Remarks:
In the experiments marked with a white asterisk (**), no bromine compound was added.
*¹Paraldehyde/3,4-diethoxytoluene (molar ratio)
*²A mixture of acetic acid in an amount of 8 mols and acetic anhydride in an amount of 2 mols per mol of the starting compound was used as solvent.
*³Air (flow rate: 100 ml/min.) was used as oxidizing agent in place of oxygen.
*⁴Cobalt (bivalent) acetylacetonate was used in place of cobalt acetate tetrahydrate.
*⁵Cobalt naphthenate (10% by weight in cobalt content) was used in place of cobalt acetate tetrahydrate.
*⁶Cobalt stearate was used in place of cobalt acetate tetrahydrate.
*⁷Cobalt nitrate hexahydrate was used in place of cobalt acetate tetrahydrate.
*⁸Cobalt benzoate was used in place of cobalt acetate tetrahydrate.
*⁹Cobalt bromide in an amount of 0.1 mol per mol of the starting compound and sodium acetate in an amount of 0.2 mol per mol of the starting compound were added instead of using cobalt acetate tetrahydrate and sodium bromide.
*¹⁰Cobalt hydroxide was used in place of cobalt acetate tetrahydrate.
*¹¹Except paraldehyde, the reaction liquid had the following composition:
3,4-diethoxytoluene: benzene: cobalt (bivalent) acetylacetonate: sodium bromide = 1: 4: 0.1: 0.01

EXAMPLE 30

Except that sodium bromide was used as bromine compound, oxidation of various compounds with oxygen was carried out in the same manner as decribed in Example 28. The results obtained are shown in Table 30. The starting compounds shown in Table 30 were synthetized as follows: A commercially available dihydroxytoluene was used as starting material and methylated or ethylated in the same manner as described in Example 28. The propylation or butylation of the starting material were carried out according to a usual manner by heating the starting material and propyl bromide or butyl bromide together with potassium hydroxide in an amount of 3 mols per mol of the starting material and a small amount of copper powder. The compounds thus obtained were sufficiently purified before use in the same manner as described in Example 28.

TABLE 30

| Starting compound | Reaction temperature (°C.) | Reaction time (min.) | Conversion rate (%) | Rate of selection (mol %) | | |
|---|---|---|---|---|---|---|
| | | | | Aldehyde | Alcohol | Acetic ester |
| 2,3-Dimethoxytoluene[*1] | 80–82 | 30 | 48.2 | 28.6 | 0.1 | 0.1 |
| 2,3-Dimethoxytoluene[*1] | 68–72 | 30 | 44.3 | 32.8 | 0.1 | 0.1 |
| 2,3-Diethoxytoluene | 70–72 | 30 | 40.6 | 31.2 | 0.1 | 0.1 |
| 3-Methoxy-4-ethoxytoluene[*2] | 74–76 | 45 | 37.7 | 43.7 | 0.7 | 3.6 |
| 3,4-Di-n-propoxytoluene | 84–86 | 60 | 31.4 | 38.1 | 0.5 | 1.1 |
| 2,3-Di-n-butoxytoluene | 98–103 | 60 | 26.1 | 24.4 | 0.1 | 0.1 |
| 3-Methoxy-4-n-octyloxytoluene[*2] | 100–102 | 60 | 28.7 | 26.5 | 0.7 | 8.4 |
| 3-Methoxy-4-n-butoxytoluene[*2] | 110–115 | 360[*3] | 31.4 | 37.9 | 0.1 | 10.3 |
| (Comparative Example)[*4] | | | | | | |
| 2,3-Dimethoxytoluene | 110–116 | 120 | 11.1 | 8.6 | 0.5 | 4.8 |
| 2,3-Di-n-butoxytoluene | 105–110 | 120 | 3.6 | 4.7 | 0.1 | 2.2 |
| 3,4-Di-n-propoxytoluene | 115–117 | 120 | 16.0 | 12.5 | 0 | 4.4 |
| 3-Methoxy-4-n-octyloxytoluene[*2] | 111–117 | 180 | 4.2 | 2.3 | 1.1 | 3.7 |
| 3-Methoxy-4-n-butoxytoluene[*2] | 116–118 | 240 | 12.4 | 10.2 | 0.1 | 2.7 |

Remarks:
[*1] Paraldehyde was not added.
[*2] These compounds are synthetized according to a usual method by using a commercially available 2-methoxy-4-methylphenol as starting material and O-ethylating it with diethyl sulfate or O-butylating or O-octylating the starting material with the corresponding bromide and then fully purified before use in the above mentioned manner.
[*3] Air (flow rate: 100 ml/min.) was used as oxidizing agent.
[*4] In Comparative Examples, sodium bromide and paraldehyde were excluded from the starting compound mixture of the present invention.

EXAMPLE 31

In a 300 ml SUS-316 stainless steel autoclave equipped with a stirrer, a thermometer and a gas inlet was placed a total amount of 150 ml of given amounts of 3,4-diethoxytoluene, cobalt acetate tetrahydrate, acetic acid, sodium bromide and paraldehyde. The liquid mixture was heated to a predetermined temperature while stirring it vigorously at a rotating speed of 1600 rpm. From a pressure tank oxygen was introduced through a pressure regulator into the autoclave to maintain the oxygen pressure at a given value. As soon as the gaseous oxygen was introduced, a violent oxidation reaction took place so that it was difficult to maintain the reaction temperature at a definite value. However, careful attention was paid to maintain the reaction temperature as definite as possible by warming or cooling and the quantity of oxygen consumed was roughly calculated from decrease in the pressure of oxygen in the oxygen pressure tank. At the time an almost required quantity of oxygen was absorbed, the reactor was quickly cooled to stop the reaction. The reaction liquid was analyzed in the same manner as described in Example 28. The results obtained are shown in Table 31 wherein the reaction temperature shows the predetermined value and the maximum value.

TABLE 31

| Exp. No. | Molar ratio to starting material | | | | Reaction temperature (°C.) | Reaction pressure (kg/cm$^2$) | Reaction time (min:sec) | Conversion rate (%) | Rate of selection (mol %) | | |
|---|---|---|---|---|---|---|---|---|---|---|---|
| | AcOH | Co | NaBr | paraldehyde | | | | | Aldehyde | Alcohol | Acetic ester |
| 1 | 12.5 | 0.3 | 0.03 | 0 | 110–113 | 2 | 13.00 | 42.2 | 36.4 | 0.4 | 9.0 |
| 2 | " | " | " | " | 115–121 | 5 | 0.50 | 29.6 | 42.1 | 0.2 | 8.9 |
| 3 | " | " | " | " | 117–124 | 20 | 0.45 | 40.8 | 52.0 | 0.2 | 11.2 |
| 4 | " | " | " | " | 116–123 | 40 | 0.40 | 47.9 | 49.3 | 0.3 | 12.2 |
| 5 | " | " | " | 0.1 | 39–41 | 20 | 45.00 | 17.6 | 7.9 | 0.8 | 4.2 |
| 6 | " | " | " | " | 48–51 | " | 30.00 | 41.2 | 31.6 | 1.6 | 5.3 |
| 7 | " | " | " | " | 67–71 | " | 15.00 | 72.5 | 38.6 | 1.0 | 7.1 |
| 8 | " | " | " | 0 | 70–71 | " | 20.00 | 25.6 | 36.0 | 0 | 6.5 |
| 9 | " | " | " | " | 102–113 | " | 1.50 | 51.6 | 45.2 | 0.2 | 8.9 |
| 10 | " | " | " | " | 135–143 | " | 0.30 | 58.3 | 52.5 | 0.3 | 9.8 |
| 11 | " | " | " | " | 149–161 | " | 0.27 | 61.9 | 51.5 | 0.7 | 12.3 |
| 12 | 0.5 | 0.03 | " | " | 135–146 | " | 1.15 | 20.3 | 8.6 | 0.3 | 9.3 |
| 13 | 1.0 | " | " | " | 134–154 | " | 0.25 | 31.1 | 36.6 | 2.0 | 3.0 |
| 14 | 5.0 | " | " | " | 132–146 | " | 0.35 | 42.2 | 48.7 | 2.1 | 4.3 |
| 15 | 12.5 | " | " | " | 132–142 | " | 0.50 | 43.8 | 50.7 | 0.3 | 6.2 |
| 16 | 15.0 | " | " | " | 131–143 | " | 0.40 | 40.9 | 47.2 | 0.2 | 5.3 |
| 17 | 3.0 | 0.001 | 0.001 | 0 | 131–136 | " | 8.00 | 35.7 | 18.9 | 0 | 4.2 |
| 18 | 12.5 | 0.1 | 0.03 | 0 | 131–154 | " | 0.44 | 67.6 | 52.2 | 0.1 | 8.7 |
| 19 | 3.0 | 0.03 | 0.00003 | 0 | 136–144 | " | 0.55 | 38.9 | 40.2 | 1.1 | 3.7 |
| 20 | 12.5 | 0.3 | 0.0003 | 0 | 134–149 | 20 | 0.40 | 57.1 | 41.2 | 0.8 | 17.3 |
| 21 | " | " | 0.003 | " | 134–160 | " | 1.00 | 83.3 | 54.9 | 0.1 | 13.0 |
| 22 | " | 0.03 | 0.5 | " | 149–162 | " | 19.30 | 40.6 | 38.4 | 0.3 | 3.0 |
| 23 | " | 0.3 | 0 | 0.1 | 121–142 | " | 1.05 | 31.4 | 38.2 | 0.1 | 13.2 |
| 24 | 12.5[*1] | 0.3 | 0.03 | 0 | 115–126 | " | 0.40 | 38.6 | 50.6 | 0.2 | 10.6[*2] |
| 25 | 12.5[*3] | 0.3 | 0.03 | " | 135–147 | " | 0.30 | 52.8 | 51.2 | 0.1 | 8.6[*4] |
| 26 | 8[*5] | " | " | " | 115–122 | " | 0.50 | 21.1 | 12.4 | 1.7 | 13.4 |
| 27 | 10[*6] | " | " | " | 115–128 | " | 0.45 | 40.6 | 49.3 | 0.9 | 16.3 |
| (Comparative Example) | | | | | | | | | | | |
| 28 | 10 | 0.1 | 0 | 0 | 160–176 | " | 0.35 | 42.2 | 27.4 | 0.1 | 0.1 |
| 29 | 12.5 | 0.3 | " | " | 150–175 | " | 0.35 | 84.1 | 36.2 | 0.1 | 11.6 |
| 30 | 12.5 | 0.3 | " | " | 145–172 | " | 0.20 | 31.7 | 38.6 | 0.1 | 12.2 |

TABLE 31-continued

| Exp. No. | Molar ratio to starting material | | | | Reaction temperature (°C.) | Reaction pressure (kg/cm$^2$) | Reaction time (min:sec) | Conversion rate (%) | Rate of selection (mol %) | | |
|---|---|---|---|---|---|---|---|---|---|---|---|
| | AcOH | Co | NaBr | paraldehyde | | | | | Aldehyde | Alcohol | Acetic ester |
| 31 | 1 | 0.0001 | 0.0001 | 0 | 132–134 | " | 15.00 | 23.1 | 2.3 | 0 | 0.5 |
| 32 | 0 | 0.03*[7] | 0.03 | 0 | 135–141 | " | 42.00 | 6.2 | 0.1 | 1.1 | 0.5 |
| 33 | 12.5 | 0.3 | 0.03 | 0.1 | 33–34 | " | 60.00 | 5.4 | 1.3 | 0.9 | 1.1 |

Remarks:
*[1]Propionic acid was used in place of acetic acid.
*[2]Propionic ester
*[3]n-Butyric acid was used in place of acetic acid.
*[4]n-Butyric ester
*[5]Acetic anhydride was used in place of acetic acid.
*[6]A mixture of acetic acid and acetic anhydride (4 mol: 1 mol in mixing ratio) was used in place of acetic acid.
*[7]Cobalt (bivalent) acetylacetonate was used in place of cobalt acetate tetrahydrate.

EXAMPLE 32

Various dihydrocarbyloxytoluenes were subjected to liquid phase oxidation under pressure conducted in the same manner as described in Example 31. The results obtained are shown in Table 32. In this example, every experiment used the starting material mixture of the following composition:

starting compound:acetic acid:cobalt acetate tetrahydrate:sodium bromide = 1:12.5:0.3:0.03 (molar ratio)

The starting compounds used in this example were synthetized in the same manner as described in Example 30.

EXAMPLE 33

To investigate the effect of paraldehyde, 3,4-dimethoxytoluene was subjected to oxidation under normal pressure in the presence of cobalt acetate tetrahydrate and paraldehyde but in the absence of a bromine compound in the same manner as described in Example 28. The results obtained are shown in Table 33. In this example, the starting compound mixture had the following composition in every experiment:

3,4-dimethoxytoluene:acetic acid:cobalt acetate tetrahydrate = 1:12.5:0.3 (in terms of molar ratio)

TABLE 32

| Exp. No. | Starting compound | Amount of *[1] paraldehyde | Reaction temperature (°C.) | Reaction pressure (kg/cm$^2$) | Reaction time (min:sec) | Conversion rate (%) | Rate of selection (mol %) | | |
|---|---|---|---|---|---|---|---|---|---|
| | | | | | | | Aldehyde | Alcohol | Acetic ester |
| 1 | 3,4-Dimethoxytoluene | 0 | 101–118 | 20 | 1:15 | 59.5 | 44.1 | 0.1 | 5.9 |
| 2 | 3,4-Dimethoxytoluene | 0 | 100–103 | 5 | 1:10 | 15.9 | 40.5 | 0.1 | 6.5 |
| 3 | 2,3-Dimethoxytoluene | 0 | 101–118 | 20 | 0:45 | 45.3 | 37.0 | 0.1 | 0.3 |
| 4 | " | 0 | 136–145 | " | 0:20 | 51.4 | 43.2 | 0.1 | 0.8 |
| 5 | " | 0.05 | 104–119 | " | 0:35 | 50.9 | 39.2 | 0.4 | 1.7 |
| 6 | 2,5-Dimethoxytoluene | 0 | 101–160*[2] | " | 90:00 | 23.8 | 16.4 | 0 | 9.2 |
| 7 | " | 0 | 116–125*[2] | 40 | 24:00 | 23.2 | 16.9 | 0 | 3.7 |
| 8 | 2,6-Dimethoxytoluene | 0 | 100–105 | 20 | 0:45 | 46.2 | 13.4 | 0 | 5.4 |
| 9 | " | 0 | 135–154 | " | 0:25 | 51.3 | 16.2 | 0 | 2.2 |
| 10 | " | 0.1 | 64–89 | " | 1:25 | 88.2 | 9.4 | 0 | 3.6 |
| 11 | " | 0.05 | 100–105 | " | 0:30 | 47.6 | 14.2 | 0 | 6.3 |
| 12 | 2,5-Diethoxytoluene | 0 | 131–160*[2] | " | 40:00 | 27.6 | 14.1 | 0 | 8.2 |
| 13 | 2,6-Di-n-propoxytoluene | 0.05 | 125–156 | " | 0:20 | 44.1 | 10.9 | 0 | 1.7 |
| 14 | 2,3-Di-n-octyloxytoluene | 0.1 | 135–161 | " | 0:55 | 48.6 | 17.3 | 0.1 | 1.1 |
| 15 | 3,4-Di-n-hexyloxytoluene | 0.1 | 120–141 | " | 0:35 | 51.3 | 22.0 | 0.1 | 2.3 |
| 16 | 3-Methoxy-4-n-hexyloxytoluene (Comparative Examples)*[3] | 0 | 110–136 | 20 | 0:50 | 48.6 | 30.1 | 0.1 | 1.7 |
| 17 | 3,4-Dimethoxytoluene | 0 | 155–174 | " | 0:40 | 40.7 | 28.0 | 0.1 | 0.1 |
| 18 | 2,3-Dimethoxytoluene | 0 | 131–135 | " | 33:00 | 15.7 | 10.7 | 0.1 | 11.5 |
| 19 | 2,5-Dimethoxytoluene | 0 | 160–180*[2] | " | 45:00 | 20.3 | 2.4 | 2.1 | 4.8 |
| 20 | 2,6-Dimethoxytoluene | 0 | 135–151 | " | 1:15 | 49.2 | 3.3 | 2.1 | 6.7 |
| 21 | 3,4-Di-n-hexyloxytoluene | 0 | 135–160 | " | 1:05 | 47.6 | 4.1 | 1.1 | 2.6 |
| 22 | 2,6-Di-n-propoxytoluene | 0 | 135–153 | " | 1:35 | 30.3 | 2.7 | 1.4 | 4.5 |
| 23 | 2,5-Diethoxytoluene | 0 | 130–160*[2] | " | 60:00 | 16.6 | 2.1 | 1.6 | 2.3 |
| 24 | 2,3-Di-n-octyloxytoluene | 0 | 135–158 | " | 1:15 | 39.2 | 1.1 | 0 | 1.8 |
| 25 | 3-Methoxy-4-n-hexyloxytoluene | 0 | 130–151 | " | 0:55 | 41.3 | 9.8 | 0.1 | 4.4 |

Remarks:
*[1]Shown in terms of molar ratio to the starting compound
*[2]As the reaction velocity was slow, the reaction temperature was gradually elevated. In the case of experiments other than those marked with *2 the reaction temperature shows the predetermined value and the maximum value.
*[3]In Comparative Examples, sodium bromide and paraldehyde were excluded from the starting compound mixture of the present invention.

TABLE 33

| Exp. No. | Amount of*[1] paraldehyde | Reaction temperature (°C.) | Reaction time (min.) | Conversion rate (%) | Rate of selection (mol %) | | |
|---|---|---|---|---|---|---|---|
| | | | | | Aldehyde | Alcohol | Acetic ester |
| 1 | 0.001 | 82–84 | 120 | 40.1 | 20.3 | 0.9 | 8.3 |
| 2 | 0.005 | 80–82 | 120 | 57.6 | 31.0 | 0.3 | 7.1 |

TABLE 33-continued

| Exp. No. | Amount of*[1] paraldehyde | Reaction temperature (°C.) | Reaction time (min.) | Conversion rate (%) | Rate of selection (mol %) | | |
|---|---|---|---|---|---|---|---|
| | | | | | Aldehyde | Alcohol | Acetic ester |
| 3 | 0.01 | 80–82 | 90 | 49.8 | 33.4 | 1.0 | 10.6 |
| 4 | 0.1 | 78–81 | 90 | 51.3 | 39.7 | 1.0 | 6.8 |
| 5 | 0.3 | 80–83 | 90 | 58.4 | 40.3 | 1.0 | 6.1 |
| 6 | 0.003*[2] | 85–87 | 90 | 48.2 | 17.6 | 0.4 | 6.2 |
| 7 | 0.5*[2] (Comparative Example) | 80–82 | 90 | 56.5 | 28.4 | 0.1 | 2.1 |
| 8 | 0 | 100–106 | 200 | 35.6 | 16.3 | 0 | 5.9 |
| 9 | 0*[2] | 110–114 | 120 | 10.7 | 6.8 | 0.1 | 4.1 |

Remarks:
*[1]Shown in terms of molar ratio to the starting compound
*[2]2,3-Diethoxytoluene was used as starting compound.

What is claimed is:

1. In the process for the production of alcohols and/or aldehydes which comprises subjecting a toluene derivative having ether radicals of the general formula selected from

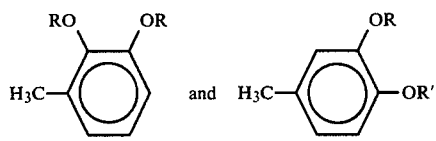

wherein R and R' are hydrocarbyl groups with 1–20 carbon atoms which may carry an inert substituent, to oxidation reaction in the liquid phase with molecular oxygen the improvement wherein the said oxidation reaction is effected under the following combination of conditions: (a) the use, as solvent, of a lower saturated fatty acid and/or anhydride thereof; (b) a partial pressure of oxygen of 0.1–50 Kg/Cm$^2$ absolute; (c) a temperature in the range of 40°–200° C.; (d) in the presence of a soluble cobalt salt in the amount of at least 0.0005 moles per mole of toluene derivative; (e) in the presence of a bromine ion-supplying substance in an amount of 0.00001–0.5 moles per mole of toluene derivative and concurrently in an amount of 0.0002–20 moles per mole of cobalt salt; (f) in such a manner that the conversion rate of said toluene derivative does not exceed 90%.

2. The improvement according to claim 1, wherein said toluene derivative is 2,3-dimethoxytoluene, 3,4-dimethoxytoluene, 2,3-diethoxytoluene, or 3,4-diethoxytoluene.

3. The improvement according to claim 1, wherein said cobalt salt is at least 0.01 moles per mole of toluene derivative, and said bromine ion-supplying substance is 0.001–0.3 moles per mole of toluene derivative and concurrently 0.001–10 moles per mole of cobalt salt.

4. The improvement according to claim 1 wherein said toluene derivative is 3,4-dimethoxytoluene or 2,3-diethoxytoluene and the oxidation reaction is effected at 40°–200° C. in the presence of at least 0.01 moles of cobalt salt per mole of toluene derivative, in the presence of 0.001–0.3 moles of bromine ion-supplying substance per mole of toluene derivative and concurrently 0.001–10 moles per mole of said cobalt salt.

5. The improvement according to claim 1 or claim 4 wherein the oxidation reaction is effected in the further presence of 0.001–0.5 moles of a co-oxidizer per mole of toluene derivative, said co-oxidizer being capable of forming a peroxy radical under the reaction conditions.

* * * * *